(12) United States Patent
Kitsunai

(10) Patent No.: US 11,219,491 B2
(45) Date of Patent: Jan. 11, 2022

(54) CENTRALIZED CONTROL APPARATUS AND METHOD OF CONTROLLING ONE OR MORE CONTROLLED APPARATUSES INCLUDING MEDICAL DEVICE

(71) Applicant: OLYMPUS CORPORATION, Tokyo (JP)

(72) Inventor: Akane Kitsunai, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/897,377

(22) Filed: Jun. 10, 2020

(65) Prior Publication Data

US 2020/0367976 A1 Nov. 26, 2020

Related U.S. Application Data

(63) Continuation of application No. PCT/JP2018/028618, filed on Jul. 31, 2018.

(30) Foreign Application Priority Data

Dec. 11, 2017 (JP) .............................. JP2017-236798

(51) Int. Cl.
*G06F 3/0484* (2013.01)
*A61B 34/00* (2016.01)
(Continued)

(52) U.S. Cl.
CPC .......... *A61B 34/25* (2016.02); *G06F 3/04842* (2013.01); *G06F 3/04847* (2013.01);
(Continued)

(58) Field of Classification Search
CPC ... A61B 34/25; A61B 2034/252; A61B 90/30; A61B 1/313; A61B 2017/00119;
(Continued)

(56) References Cited

U.S. PATENT DOCUMENTS 10,467,029 B1 * 11/2019 Lin .......................... G06F 9/451
2002/0105409 A1    8/2002 Nakamitsu et al.
(Continued)

FOREIGN PATENT DOCUMENTS

EP    1787573 A1    5/2007
EP    2087833 A2    8/2009
(Continued)

OTHER PUBLICATIONS

International Search Report dated Oct. 9, 2018 issued in PCT/JP2018/028618.

*Primary Examiner* — Michael Roswell
(74) *Attorney, Agent, or Firm* — Scully, Scott, Murphy & Presser, P.C.

(57) ABSTRACT

A system controller performs collective setting processing which collectively performs setting with respect to one or more controlled devices including a medical device. The system controller judges a degree of error relating to a state of the controlled device which occurred when the collective setting processing is performed. The system controller displays an error removing screen for removing an occurred error based on a judgement result of the degree of error. A setting instruction operation is an operation which selects a desired scene from a plurality of scenes which are set in advance corresponding to a progress of a surgery. The degree of error is associated with the plurality of scenes, and the system controller judges the degree of the occurred error based on the scene which is underway of the surgery.

10 Claims, 18 Drawing Sheets

TBLa

| DEVICE | CONTENT OF ERROR | DEGREE OF ERROR | |
|---|---|---|---|
| | | LARGE | SMALL |
| ELECTROCAUTERY | CONTACT FAILURE OF COUNTER ELECTRODE PLATE HAS OCCURRED | O | |
| | TREATMENT INSTRUMENT OTHER THAN INTENDED USE IS CONNECTED | O | |
| PROCESSOR | ENDOSCOPE OTHER THAN INTENDED USE IS CONNECTED | O | |
| | WHITE BALANCE IS NOT ADJUSTED | O | |
| | ENDOSCOPE IS NOT CONNECTED | O | |
| | INTERNAL MEMORY CAPACITY IS INSUFFICIENT | | O |
| LIGHT SOURCE APPARATUS | LIMIT OF LIFETIME OF LAMP IS NEAR | | O |
| RECORDING APPARATUS | INTERNAL HDD HAS NO REMAINING CAPACITY | | O |
| | REMAINING CAPACITY OF INTERNAL HDD IS INSUFFICIENT | | O |
| INSUFFLATOR | REMAINING AMOUNT OF CO2 CYLINDER IS LOW | | O |

(51) Int. Cl.
    *A61B 90/30*     (2016.01)
    *A61B 1/313*     (2006.01)
    *A61B 17/00*     (2006.01)
    *A61B 18/00*     (2006.01)
    *A61M 13/00*     (2006.01)

(52) U.S. Cl.
    CPC ............. *A61B 1/313* (2013.01); *A61B 90/30* (2016.02); *A61B 2017/00119* (2013.01); *A61B 2018/00595* (2013.01); *A61B 2034/252* (2016.02); *A61M 13/003* (2013.01)

(58) Field of Classification Search
    CPC ...... A61B 2018/00595; A61B 18/1206; A61B 90/98; A61B 90/361; G06F 3/04842; G06F 3/04847; A61M 13/003
    See application file for complete search history.

(56) References Cited

U.S. PATENT DOCUMENTS

| | | |
|---|---|---|
| 2007/0161861 A1 | 7/2007 | Kawai |
| 2009/0199125 A1 | 8/2009 | Sekiguchi et al. |
| 2009/0210754 A1* | 8/2009 | Sekiguchi ............. G06F 11/327 714/57 |
| 2011/0125149 A1* | 5/2011 | El-Galley ............. A61B 17/00 606/34 |
| 2011/0279268 A1 | 11/2011 | Konishi et al. |
| 2013/0060194 A1* | 3/2013 | Rotstein ............. A61M 39/284 604/151 |
| 2013/0281987 A1* | 10/2013 | Maeda ............. A61B 1/00039 606/1 |
| 2016/0275246 A1 | 9/2016 | Okusawa et al. |
| 2018/0364665 A1* | 12/2018 | Clymer ................ G05B 19/042 |

FOREIGN PATENT DOCUMENTS

| | | |
|---|---|---|
| JP | 11-299729 A | 11/1999 |
| JP | 2002-306401 A | 10/2002 |
| JP | 2006-055348 A | 3/2006 |
| JP | 2006-288956 A | 10/2006 |
| JP | 2009-183686 A | 8/2009 |
| WO | WO 2006/019137 A1 | 2/2006 |
| WO | WO 2011/052391 A1 | 5/2011 |
| WO | WO 2015/087612 A1 | 10/2014 |
| WO | WO 2017/094363 A1 | 6/2017 |

* cited by examiner

FIG. 8

TBLa

| DEVICE | CONTENT OF ERROR | DEGREE OF ERROR | |
|---|---|---|---|
| | | LARGE | SMALL |
| ELECTROCAUTERY | CONTACT FAILURE OF COUNTER ELECTRODE PLATE HAS OCCURRED | O | |
| | TREATMENT INSTRUMENT OTHER THAN INTENDED USE IS CONNECTED | O | |
| PROCESSOR | ENDOSCOPE OTHER THAN INTENDED USE IS CONNECTED | O | |
| | WHITE BALANCE IS NOT ADJUSTED | O | |
| | ENDOSCOPE IS NOT CONNECTED | O | |
| | INTERNAL MEMORY CAPACITY IS INSUFFICIENT | | O |
| LIGHT SOURCE APPARATUS | LIMIT OF LIFETIME OF LAMP IS NEAR | | O |
| RECORDING APPARATUS | INTERNAL HDD HAS NO REMAINING CAPACITY | | O |
| | REMAINING CAPACITY OF INTERNAL HDD IS INSUFFICIENT | | O |
| INSUFFLATOR | REMAINING AMOUNT OF CO2 CYLINDER IS LOW | | O |

TBLb

|  | TOTAL | LAST TIME | TIME BEFORE LAST | ... | FIRST TIME |
|---|---|---|---|---|---|
| FUNCTION A | 100 | 3 | 2 | ... | 2 |
| FUNCTION B | 25 | 0 | 1 | ... | 0 |
| FUNCTION C | 10 | 0 | 0 | ... | 0 |
| FUNCTION D | 30 | 1 | 0 | ... | 1 |
| ⋮ | ⋮ | ⋮ | ⋮ | ⋮ | ⋮ |

FIG. 15

TBLa1

| DEVICE | CONTENT OF ERROR | DEGREE OF ERROR | | |
|---|---|---|---|---|
| | | LARGE | INTERMEDIATE | SMALL |
| ELECTROCAUTERY | CONTACT FAILURE OF COUNTER ELECTRODE PLATE HAS OCCURRED | O | | |
| ELECTROCAUTERY | TREATMENT INSTRUMENT OTHER THAN INTENDED USE IS CONNECTED | O | | |
| PROCESSOR | ENDOSCOPE OTHER THAN INTENDED USE IS CONNECTED | O | | |
| | WHITE BALANCE IS NOT ADJUSTED | O | | |
| | ENDOSCOPE IS NOT CONNECTED | | O | |
| | INTERNAL MEMORY CAPACITY IS INSUFFICIENT | | | O |
| LIGHT SOURCE APPARATUS | LIMIT OF LIFETIME OF LAMP IS NEAR | | | O |
| RECORDING APPARATUS | INTERNAL HDD HAS NO REMAINING CAPACITY | | O | |
| | REMAINING CAPACITY OF INTERNAL HDD IS INSUFFICIENT | | O | O |
| INSUFFLATOR | REMAINING AMOUNT OF CO2 CYLINDER IS LOW | | O | O |

CENTRALIZED CONTROL APPARATUS AND METHOD OF CONTROLLING ONE OR MORE CONTROLLED APPARATUSES INCLUDING MEDICAL DEVICE

CROSS REFERENCE TO RELATED APPLICATION

This application is a continuation application of PCT/JP2018/028618 filed on Jul. 31, 2018 and claims benefit of Japanese Application No. 2017-236798 filed in Japan on Dec. 11, 2017, the entire contents of which are incorporated herein by this reference.

BACKGROUND OF THE INVENTION

1. Field of the Invention

The present invention relates to a centralized control apparatus and a method of controlling one or more controlled apparatuses including a medical device, and more particularly to a centralized control apparatus and a method of controlling one or more controlled devices including a medical device in a centralized manner.

2. Description of the Related Art

Conventionally, various medical devices and various non-medical devices are installed in an operation room. Such various devices may include a shadowless lamp, an endoscope apparatus, and an insufflator, for example. A system controller as a centralized control apparatus communicates with such various devices, and performs setting of set values and a centralized control with respect to the various devices.

An operation panel apparatus is connected to the system controller. When a surgery starts, a surgeon, a nurse or the like operates the operation panel apparatus so as to operate a desired device or to set or change various preset values.

The operations applied to each device include instructions to allow the device to perform or stop functions which the device has, setting relating to functions and the like, and users of various devices such as a surgeon, a nurse and the like display operation screens for such operations on an operation panel apparatus, and perform desired operations.

When a surgery starts, various settings are made with respect to the respective devices corresponding to a stage or a scene of the surgery, and the user performs the surgery by instructing desired devices to perform operations.

The number of devices used in the surgery is not so small and hence, a plurality of settings are made with respect to the plurality of devices in each scene, and such setting is cumbersome and time-consuming.

In view of the above-mentioned circumstances, for example, as disclosed in International Publication No. WO 2017/094363, there has been proposed a system controller having a preset function by which a user can collectively set a plurality of predetermined set values with respect to a plurality of predetermined devices. After collectively setting the plurality of predetermined set values, the user can immediately perform the operations of the devices corresponding to a stage or a scene of the surgery.

There may be a case where some error occurs at the time of collectively setting the plurality of predetermined set values. In such a case, a user removes the error. However, even in the case where an error occurs, when a degree of error is small so that it is unnecessary to rapidly remove the error, there may be a case where the user continues the treatment without immediately removing the error. On the other hand, in the case where such error does not occur, the user can perform the operations of desired devices.

SUMMARY OF THE INVENTION

According to an aspect of the present invention, there is provided a centralized control apparatus including a processor, the processor being configured to: perform collective setting processing by receiving an instruction operation which collectively performs setting with respect to one or more controlled devices including a medical device, judge a degree of error relating to a state of the one or more controlled devices which occurs when the collective setting processing is performed due to a setting instruction operation performed with respect to the one or more controlled devices; and control so as to display an error removing screen for removing an occurred error based on a judgement result of the degree of error, the setting instruction operation being an operation for selecting a desired scene from a plurality of scenes set in advance corresponding to a progress of a surgery, the degree of error being associated with the plurality of scenes, the processor judging a degree of the occurred error based on a scene which is underway in the surgery.

According to an aspect of the present invention, there is provided a method of controlling one or more controlled apparatuses including a medical device, the method including: performing collective setting processing by receiving an instruction operation which collectively performs setting with respect to the one or more controlled devices; judging a degree of error which occurs when the collective setting processing is performed due to a setting instruction operation performed with respect to the one or more controlled devices in a state where the degree of error is associated with states of the one or more controlled devices and a plurality of scenes which are underway in a surgery; and performing a control such that an error removing screen for removing an occurred error is displayable based on a judgement result of the degree of error, wherein the setting instruction operation is an operation which selects a desired scene from a plurality of scenes which are set in advance corresponding to a progress of a surgery, the degree of error is associated with the plurality of scenes, and the degree of the occurred error is judged based on a scene which is underway in the surgery.

BRIEF DESCRIPTION OF THE DRAWINGS

FIG. 8 is a view showing the configuration of a table in a degree-of-error information storing section according to the embodiment of the present invention;

FIG. 15 is a view showing the configuration of a table of a degree-of-error information storing section according to a modification 2 of the embodiment of the present invention;

DETAILED DESCRIPTION OF THE PREFERRED EMBODIMENT

Hereinafter, an embodiment of the present invention is described with reference to drawings.
(Configuration of System)

Figure 1:
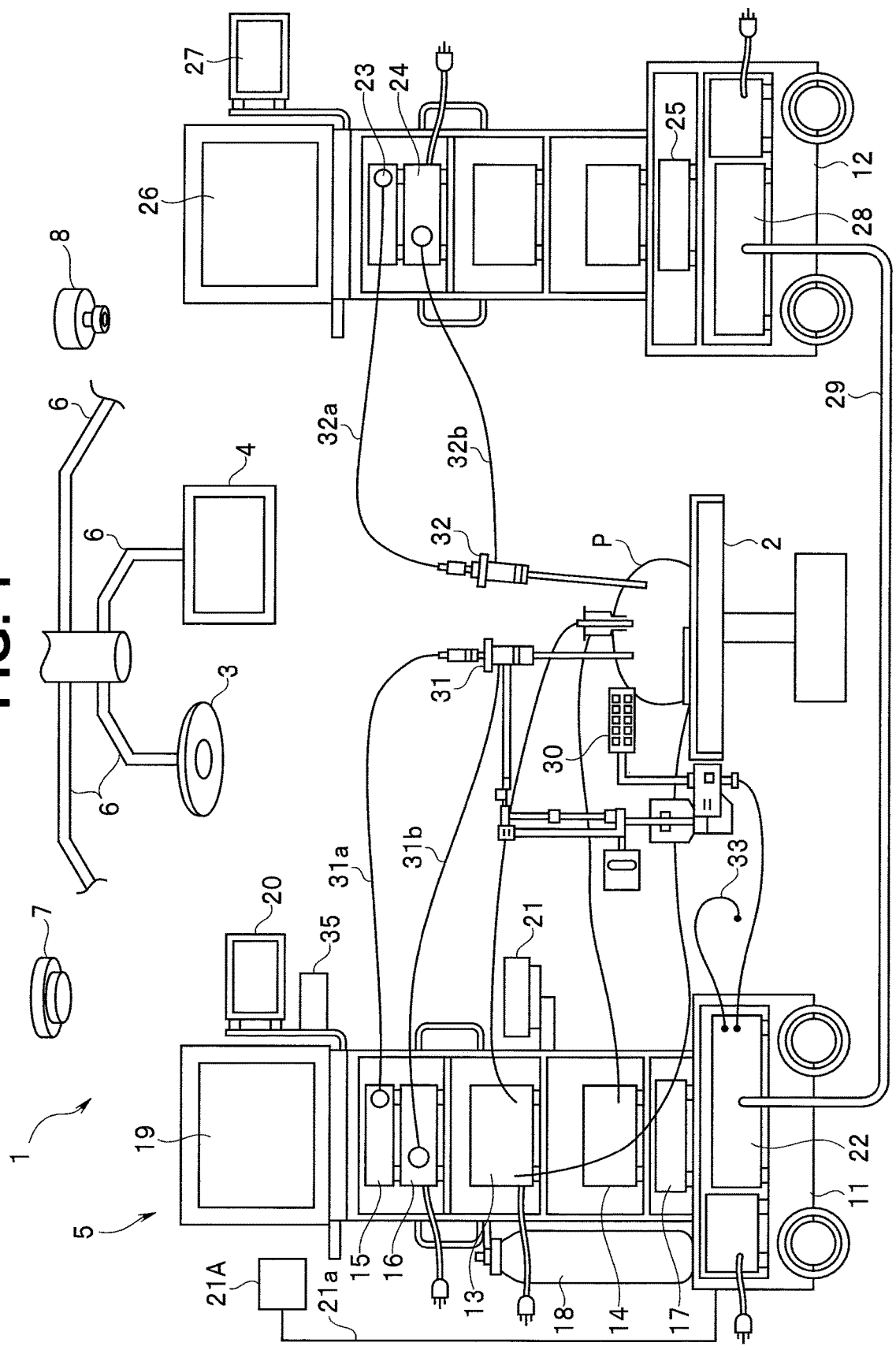
FIG. 1 is a configurational view of a surgery system according to an embodiment of the present invention.

First, the entire configuration of a surgery system 1 disposed in an operation room is described with reference to FIG. 1. FIG. 1 is a configurational view of the surgery system 1 according to the embodiment of the present invention. The surgery system 1 includes a plurality of medical devices such as an endoscope, and a plurality of non-medical devices such as a shadowless lamp.

As shown in FIG. 1, in the operation room, an operating table 2 on which a patient P lies, the plurality of shadowless lamps 3, a display apparatus 4, and a medical system 5 are disposed. The medical system 5 has a first cart 11 and a second cart 12. The respective shadowless lamps 3 and the display apparatus 4 are fixed to a ceiling of the operation room by arms 6. A room light 7 is further disposed on the ceiling in the operation room. A surgery field camera 8 and a room camera not shown are also disposed in the operation room.

On the first cart 11, as medical devices which are controlled apparatuses, an electrocautery apparatus 13, an insufflator 14, a video processor 15, a light source apparatus 16, a recorder 17 for recording, and a gas cylinder 18 filled with carbon dioxide are mounted. The video processor 15 is connected to a first endoscope 31 via a camera cable 31a.

The light source apparatus 16 is connected to the first endoscope 31 via a light guide cable 31b. The display apparatus 19, a first centralized display panel 20, an operation panel apparatus 21 and the like are mounted on the first cart 11. The display apparatus 19 displays an endoscope image and the like. For example, display apparatus 19 is a TV monitor.

The recorder 17 is a recording apparatus which includes a large capacity storage apparatus such as a hard disk drive apparatus.

The centralized display panel 20 serves as display means capable of selectively displaying all data during a surgery. The operation panel apparatus 21 is constituted of: a display section such as a liquid crystal display; and a touch panel integrally mounted on the display section, for example. The operation panel apparatus 21 serves as a centralized operation apparatus which is operated by a nurse or the like in a non-sterilized region.

A system controller 22 serving as a centralized control apparatus is mounted on the first cart 11. To the system controller 22, the respective shadowless lamps 3, the room light 7, the electrocautery apparatus 13, the insufflator 14, the video processor 15, the light source apparatus 16, the recorder 17 and the like described above are connected via communication lines not shown. A head set type microphone 33 can be connected to the system controller 22 and hence, the system controller 22 can recognize a voice inputted from the microphone 33, and can control the respective devices in accordance with a voice from a surgeon.

To the system controller 22, a second operation panel apparatus 21A which is mounted on a wall of the operation room is also connected via a cable 21a. A nurse or the like in the non-sterilized region can perform operations of various devices also using the operation panel apparatus 21A.

The first cart 11 includes a RFID (radio frequency identification) terminal 35 which can read and write ID information by wireless for identifying objects based on ID tags embedded in the first endoscope 31, a treatment instrument of the electrocautery apparatus 13 and the like.

On the other hand, a video processor 23, a light source apparatus 24, an image processing apparatus 25, a display apparatus 26 and a centralized display panel 27, which are controlled apparatuses, are mounted on the second cart 12. The video processor 23 is connected to a second endoscope 32 via a camera cable 32a. The light source apparatus 24 is connected to the second endoscope 32 via a light guide cable 32b.

The display apparatus 26 displays an endoscope image or the like which is captured by the video processor 23. The centralized display panel 27 can selectively display all data during a surgery.

The video processor 23, the light source apparatus 24, the image processing apparatus 25 and the like are connected to a relay unit 28 mounted on the second cart 12 via communication lines not shown. The relay unit 28 is connected to the system controller 22 mounted on the above-mentioned first cart 11 via a relay cable 29.

In this manner, the system controller 22 can control the video processor 23, the light source apparatus 24, and the image processing apparatus 25 and the like mounted on the second cart 12, and the electrocautery apparatus 13, the insufflator 14, the video processor 15, the light source apparatus 16 and the recorder 17 mounted on the first cart 11, the respective shadowless lamps 3, the respective display apparatuses 4 and room lamps (not shown) and the like by a centralized control.

Accordingly, when communication is made between the system controller 22 and these apparatuses, the system controller 22 can display a setting state of the connected apparatuses and a setting screen of operation switches and the like on the liquid crystal displays of the above-mentioned operation panel apparatuses 21 and 21A. The system controller 22 can perform inputting of operations such as a change of a set value due to an operation of a touch panel in a predetermined region when a user touches the desired operation switch.

The remote controller 30 is a second centralized operation apparatus which a surgeon or the like in a sterilized region operates, and the remote controller 30 can operate other apparatuses with which communication is established via the system controller 22.

An infrared communication port (not shown) which is communication means is mounted on the system controller 22. The infrared communication port is disposed at the position to which infrared rays can be easily irradiated such as an area in the vicinity of the display apparatus 19. The infrared communication port is connected with the system controller 22 by a cable.

(Configuration of System Controller)

Figure 2:
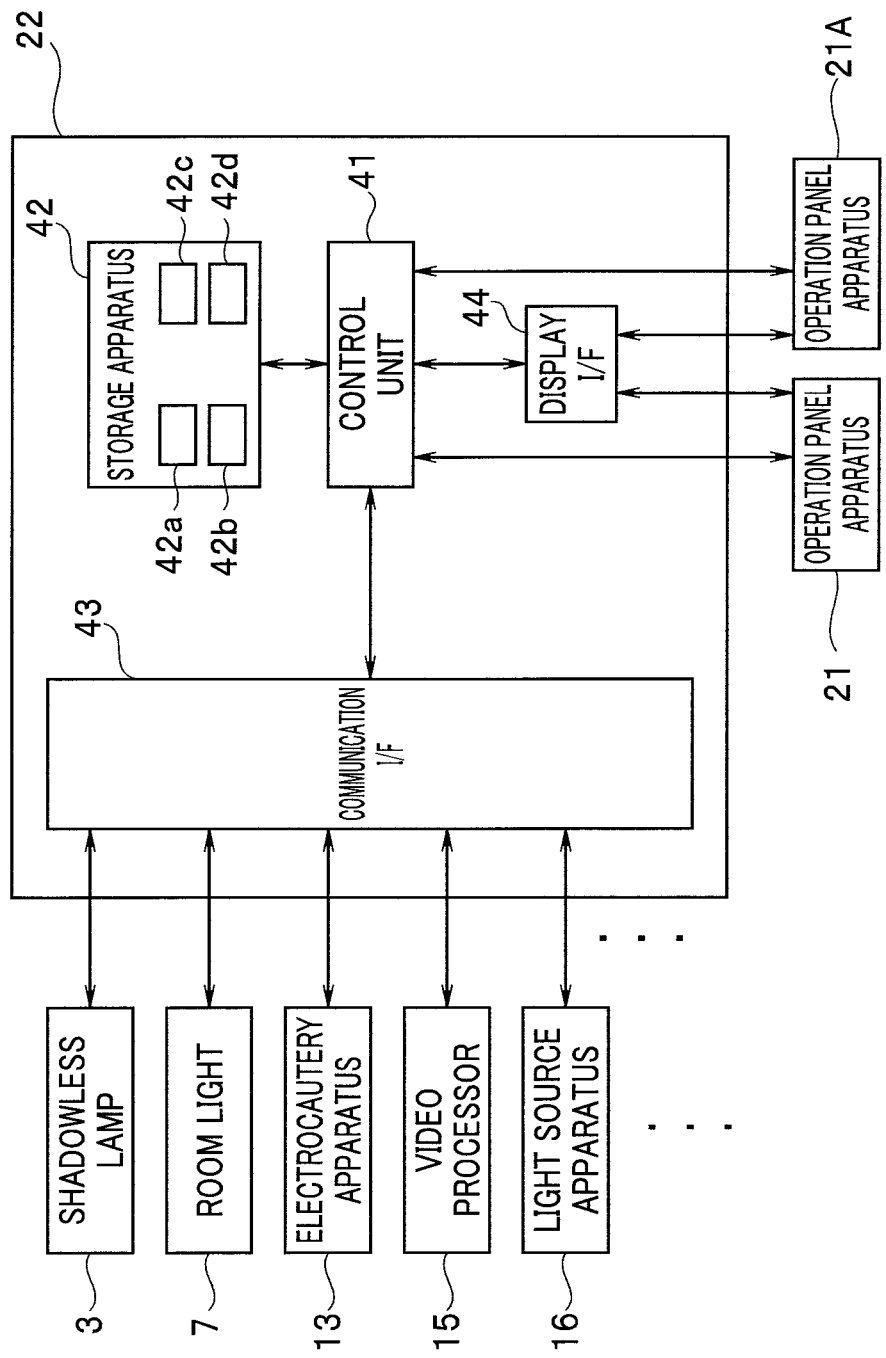
FIG. 2 is a block diagram showing the configuration of a system controller according to the embodiment of the present invention.

FIG. 2 is a block diagram showing the configuration of the system controller 22.

The system controller 22 includes a control unit 41, a storage apparatus 42, a communication interface (hereinafter, abbreviated as communication I/F) 43, and a display interface (hereinafter referred as display I/F) 44.

The control unit 41 includes a central processing unit (hereinafter referred to as CPU), a ROM, a RAM and the like. The control unit 41 reads and executes software programs of various functions which the CPU records in the ROM thus performing various functions which the system controller 22 has.

The storage apparatus 42 is a nonvolatile rewritable storage apparatus such as a flash memory or a hard disk apparatus. The software programs for performing various functions of the system controller 22 are also stored in the storage apparatus 42, and the CPU of the control unit 41 can read and execute such software programs.

The storage apparatus 42 includes a program storing section 42*a* which stores the software programs for various functions including a program for display processing of an operation screen described later.

The software programs stored in the program storing section 42*a* includes, besides control programs for controlling operations of various devices included in the surgery system 1, a collective setting processing program for performing collective setting processing for every scene, a screen generating program for generating various screens such as operation screens for designated functions, a history information recording program for recording operation log information and the like which are described later.

The storage apparatus 42 includes the setting information storing section 42*b* which stores various setting information of a plurality of devices for every scene described later. In the set information storing section 42*b*, set values with respect to the respective devices used in every scene are set in advance by a user.

Specifically, the setting information storing section 42*b* stores information on the set values (hereinafter also referred to as set information) with respect to one or more devices used in the scene for every scene. The set values are, for example, turning on or off of the devices, output values, threshold values and the like.

When a user selects a scene, the control unit 41 reads set information of the respective devices with respect to the selected scene from the set information storing section 42*b*, and executes a collective set processing program to be set to the plurality of corresponding devices.

The storage apparatus 42 includes a history information storing section 42*c* as an operation log information storing section which stores operation information on operations performed by a user with respect to one or more controlled devices as operation log information.

As described later, a user selects a scene, and performs a surgery by operating the operation panel apparatuses 21 and 21A while operating desired devices. Accordingly, in the history information storing section 42*c*, along with a lapse of time, history information of operations performed by the user is stored as operation log information.

As described later, based on operation log information stored in the history information storing section 42*c*, an operation screen with high frequency of use is extracted after the execution of collective setting for every scene.

The storage apparatus 42 includes an error degree information storing section 42*d* which stores information on a degree of error for every error with respect to various errors generated in collective setting. The degrees of errors for every error are set and stored in advance in the error degree information storing section 42*d* by the user. The configuration of the error degree information storing section 42*d* is described later.

The set information storing section 42*b* and history information storing section 42*c* respectively store set information and history information for every surgery and every surgeon.

The communication I/F 43 is an interface circuit to which a plurality of communication lines connected to the plurality of devices are connected, and performs communication between the control unit 41 and the respective devices. In FIG. 2, among the plurality of devices, the shadowless lamps 3, the room light 7, the electrocautery apparatus 13, the video processor 15, and the light source apparatus 16 are shown. Accordingly, the control unit 41 performs turning on or off of the respective devices, setting or changing of set values, acquisition of operation states or the like of the respective devices and the like with communication with the respective devices via the communication I/F 43.

The control unit 41 receives operation signals from the operation panel apparatuses 21 and 21A, and outputs image signals of operation screens to be displayed on the liquid crystal displays of the operation panel apparatuses 21 and 21A to the operation panel apparatuses 21 and 21A via a display I/F 44.

A surgeon, a nurse or the like (hereinafter referred to as a user) displays a home screen and an operation screen for performing functions which the respective devices have on the display screen of the operation panel apparatus 21 or 21A, and instructs the respective medical devices and non-medical devices of the surgery system 1 to perform the functions by touching various operation buttons displayed on the operation screen.

As described later, the user, on the display screen of the operation panel apparatus 21 or 21A, can instruct performing of collective setting of the respective devices by selecting a scene or can receive notification of error information at the time of performing collective setting.

These operations by the user with respect to the operation panel apparatus 21 or 21A are recorded in the history information storing section 42c as operation log information.

The home screen and the various operation screens can be displayed on both the operation panel apparatus 21 and the operation panel apparatus 21A connected to the system controller 22, and the user can use either one of these operation panel apparatuses. However, the description is made with respect to the case where the home screen and the various operation screens are displayed on the operation panel apparatus 21 hereinafter.

(Manner of Operation)

Next, collective setting processing of the system controller 22 in the above-mentioned surgery system 1 is described.

First, the configuration of the home screen which is a top menu of an operation screen displayed on the display section of the operation panel apparatus 21 is described.

Figure 3:
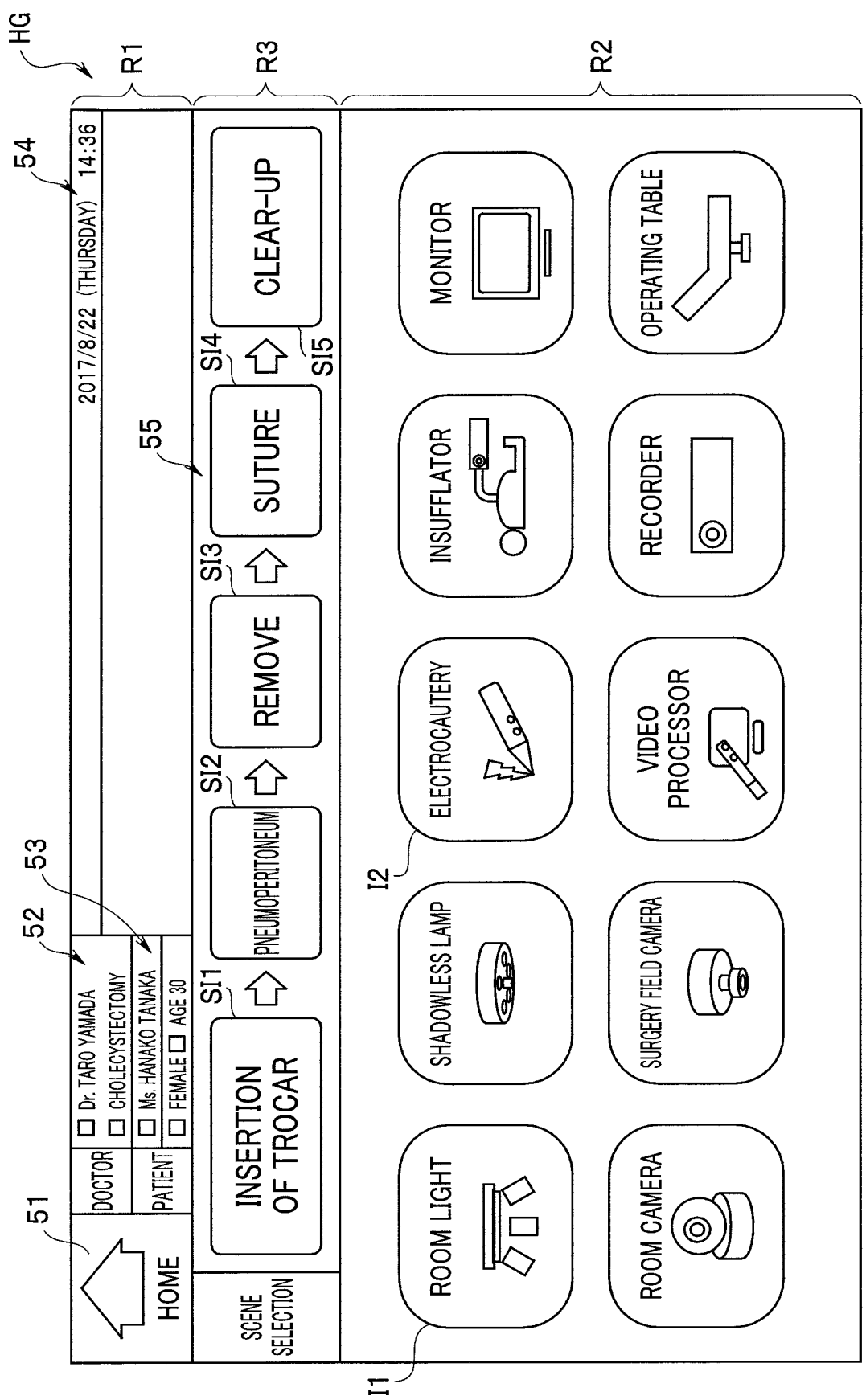
FIG. 3 is a view showing an example of a home screen displayed on a display section of an operation panel apparatus according to the embodiment of the present invention.

FIG. 3 is a view showing an example of the home screen displayed on the display section of the operation panel apparatus 21.

The home screen HG shown in FIG. 3 and the respective operation screens described hereinafter are displayed on the display section of the liquid crystal display or the like of the operation panel apparatus 21. A user performs a surgery by selecting a desired device or a desired scene from the home screen HG.

The home screen HG has, within a rectangular display region, an upper region R1, a lower region R2 and an intermediate region R3 sandwiched between the upper region R1 and the lower region R23.

The upper region R1 has a home button 51, a doctor/surgery method display section 52 where a doctor and a surgery method are displayed, a patient information display section 53 where the name, the sex, and the age of a patient are displayed, and a time display section 54 where current year, month, day and time are displayed.

The home button 51 is an operation section which is used for displaying the home screen HG which is the top screen shown in FIG. 3. The operation panel apparatus 21 has the touch panel and hence, when the user touches the home button 51 with his/her finger or the like, the system controller 22 judges that the home button 51 is operated, displays the home screen HG on the operation panel apparatus 21.

The home button 51 is always displayed at the same position also in other operation screens and hence, the user can immediately display the home screen HG at any time.

The doctor/surgery method display section 52 is a region where the name of a doctor who is in charge of a surgery which is going to be performed or currently being performed and the name of a surgery method are displayed. The name of the doctor and the name of the surgery method are displayed based on information set in the system controller 22.

The patient information display section 53 is a region where the name, the sex and the age of a patient who is going to have a surgery from now or is currently having a surgery are displayed, and the name, the sex and the age of the patient are displayed based on information set in the system controller 22.

The time display section 54 is a region where time information which the system controller 22 has is displayed, and the time information includes the year, the month, the date and the time.

The lower region R2 displays a plurality of icons with respect to the plurality of devices relating to a surgery. A user can select a device to be operated or to be set by touching the icon corresponding to the device. When the user touches the icon, an operation screen of the device corresponding to the touched icon is displayed on the operation panel apparatus 21.

As shown in FIG. 1, a larger number of apparatuses are disposed in the operation room. Accordingly, although not shown, for displaying a plurality of apparatuses which cannot be displayed in the lower region R2, a scrolling function for the lower region R2, an operation button for a page turning function and the like are also provided.

For example, when the user touches the icon I1 of the room light 7, an operation screen of the room light 7 is displayed in the lower region R2, and the user can perform or stop various functions of the room light 7 such as an ON/OFF operation or setting of a dimming level.

When the user touches the icon I2 of the electrocautery apparatus 13, an operation screen of the electrocautery apparatus 13 is displayed in the lower region R2, and the user can perform or stop various functions of the electrocautery apparatus 13 such as an ON/OFF operation or setting of an output level.

The intermediate region R3 includes a scene selection operation section 55 which allows the user to select a scene in a surgery.

In the embodiment, the scene selection operation section 55 in the intermediate region R3 is displayed not only on the home screen HG but also on any operation screen changed from the home screen HG.

A plurality of icons which indicate a plurality of scenes are displayed on the scene selection operation section 55. In FIG. 3, five icons SI1 to SI5 for selecting five scenes are displayed. Five icons SI1 to SI5 are arranged along a progress of a surgery. In this case, the icons are arranged in a state where time elapses from a left side to a right side, and five icons correspond to five scenes from the first scene "insertion of trocar" to the last scene "clear-up".

When the user selects a desired icon from the plurality of icons displayed on the scene selection operation section 55, collective setting processing is performed with respect to the scene which corresponds to the selected icon.

In the case shown in FIG. 3, "cholecystectomy" displayed in the doctor/surgery method display section 52 has five scenes. When the user firstly selects "insertion of a trocar" by touching the icon SI1, collective setting processing for the scene "insertion of trocar" is performed. Then, treatment or the like applied to a patient is performed by operating the respective devices.

When the scene "insertion of trocar" is finished, the user touches the icon SI2 "pneumoperitoneum" so that collective setting processing for the scene "pneumoperitoneum" is performed. Then, the treatment or the like applied to the patient is performed by operating the respective devices.

Hereinafter, in the same manner, the user performs the scenes including "remove", "suture", and "clear-up" in this order, and the surgery is finished.

When the collective setting processing is performed with respect to the selected scene, a plurality of set information which are set in advance are read from the set information storing section 42b, and such set information are set in one or more devices. The respective icons SI1 to SI5 of the scene selection operation section 55 are setting instruction operation buttons for instructing performing of the collective setting processing.

In other words, the respective setting instruction operations which instruct performing of the collective setting processing are operations which select the scene set corresponding to the progress of the surgery from the plurality of scenes.

The user can perform a surgery on a patient by operating various devices after selecting the scene.

However, when an unexpected error occurs at the time of performing collective setting functions, the user has to perform an operation for removing such an error. When the degree of error is small, there may also be a case where treatment or the like is performed without removing the error. Further, there may also be a case where the user performs treatment or the like by operating the devices which are not collectively set or by operating the collectively set devices.

Conventionally, when an error occurs, it is necessary for the user to return to the home screen for removing the error by operating the operation panel apparatus, to find out and display the operation screen for removing the error in a device in which the error occurs, and to apply an operation to the device. Accordingly, it is necessary for the user to perform an operation screen change operation which takes time and efforts.

When there is a device which the user wants to use additionally after the collective setting function is performed, it is necessary for the user to return to the home screen by operating the operation panel apparatus, to find out and display an operation screen of the device which the user wants to use on the screen, and to apply an operation to the device. Accordingly, it is necessary for the user to perform an operation screen change operation which takes time and efforts.

In the embodiment, as described hereinafter, by setting a degree of error in advance, when an error occurs at the time of performing a collective setting function, only an error which is required to be removed is immediately removed. On the other hand, when the error is removed, when an error does not occur or when a degree of error is small, an operation can be immediately performed on a device which the user wants to use additionally after a collective setting function is performed.

When a surgery starts, a history information recording program is also executed, and collection and storing of operation log information from starting to finishing of the surgery are performed.

Figure 4:
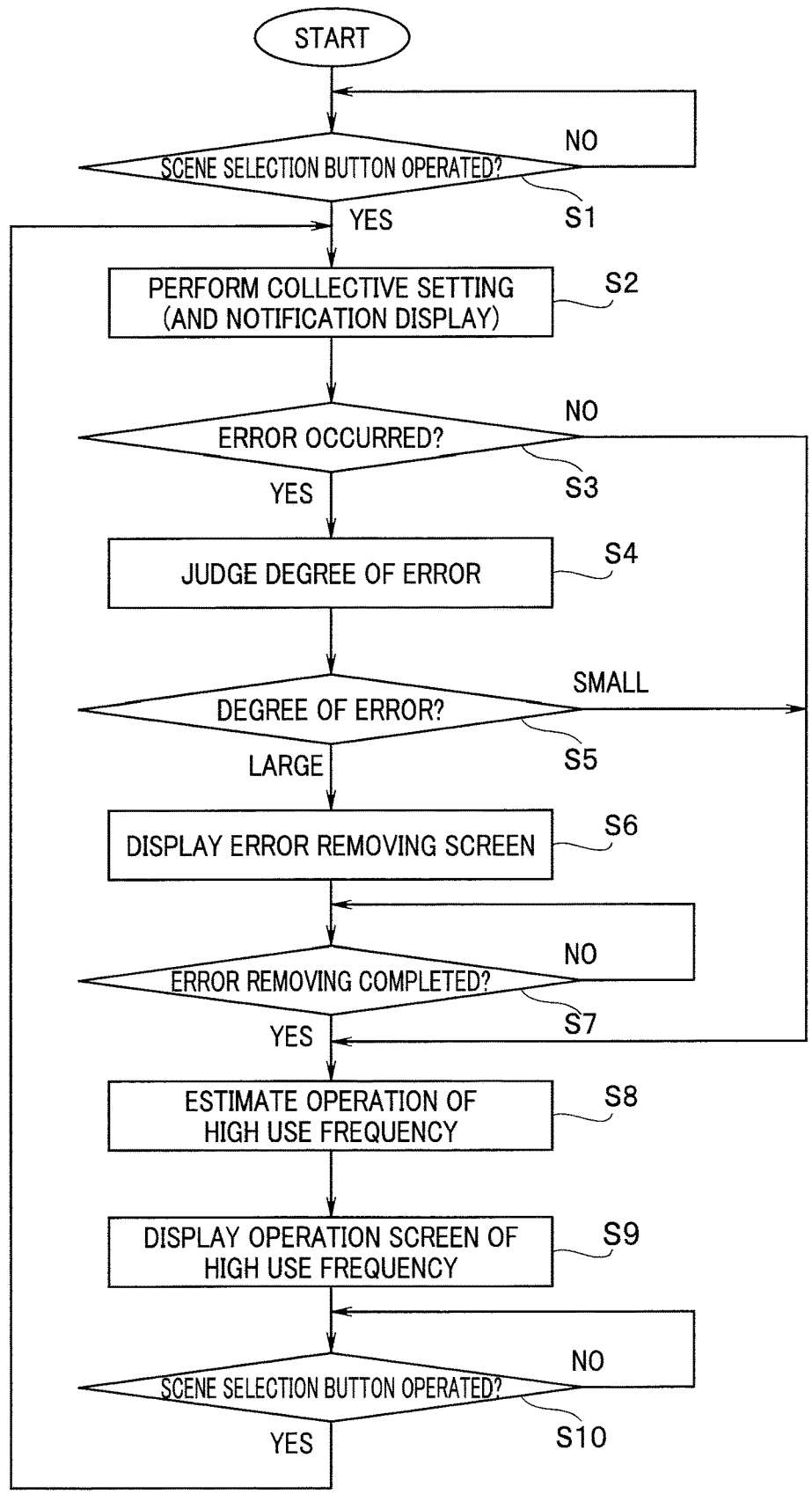
FIG. 4 is a flowchart showing an example of a flow of processing at the time of performing a scene selection according to the embodiment of the present invention.
Figure 5:
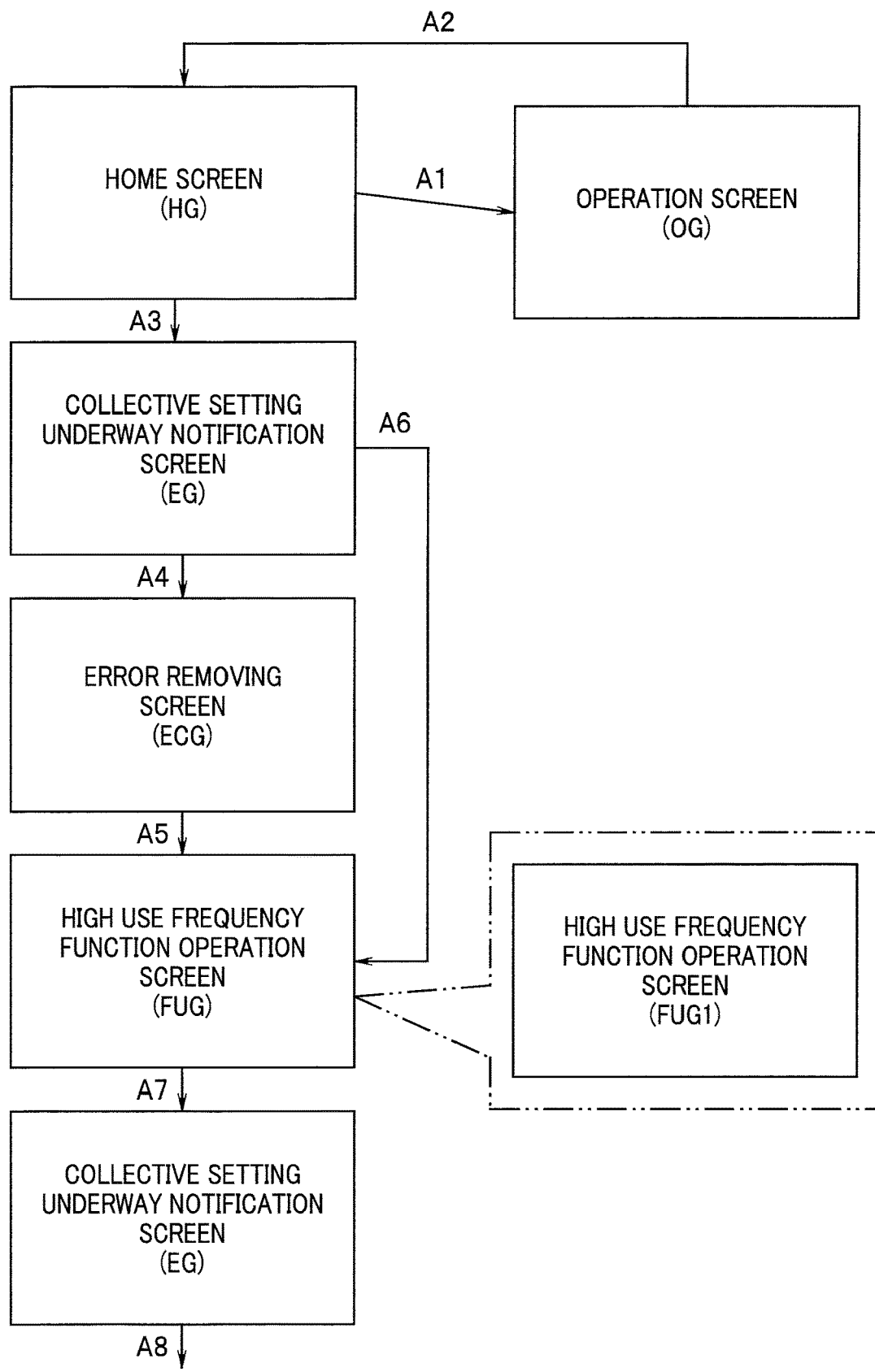
FIG. 5 is a screen transition chart showing a transition of an operation screen according to the embodiment of the present invention.

FIG. 4 is a flowchart showing an example of the flow of processing at the time of performing selection of a scene. FIG. 5 is a screen change chart showing a change of an operation screen. A processing program shown in FIG. 4 is stored in the program storing section 42a or the ROM of the control unit 41, and is read and executed by the CPU of the control unit 41.

Hereinafter, the processing shown in FIG. 4 is described by taking the scene displayed on the scene selection operation section 55 shown in FIG. 3 as an example.

When the home screen HG is displayed on the operation panel apparatus 21, the user is in a state where the user can select a scene on the scene selection operation section 55 and, simultaneously, the user is in a state where the user can also apply an operation to the device displayed on the lower region R2. Accordingly, when the user selects any one of the plurality of icons with respect to the device displayed in the lower region R2, an operation screen of the selected device is displayed in the operation panel apparatus 21.

Figure 6:
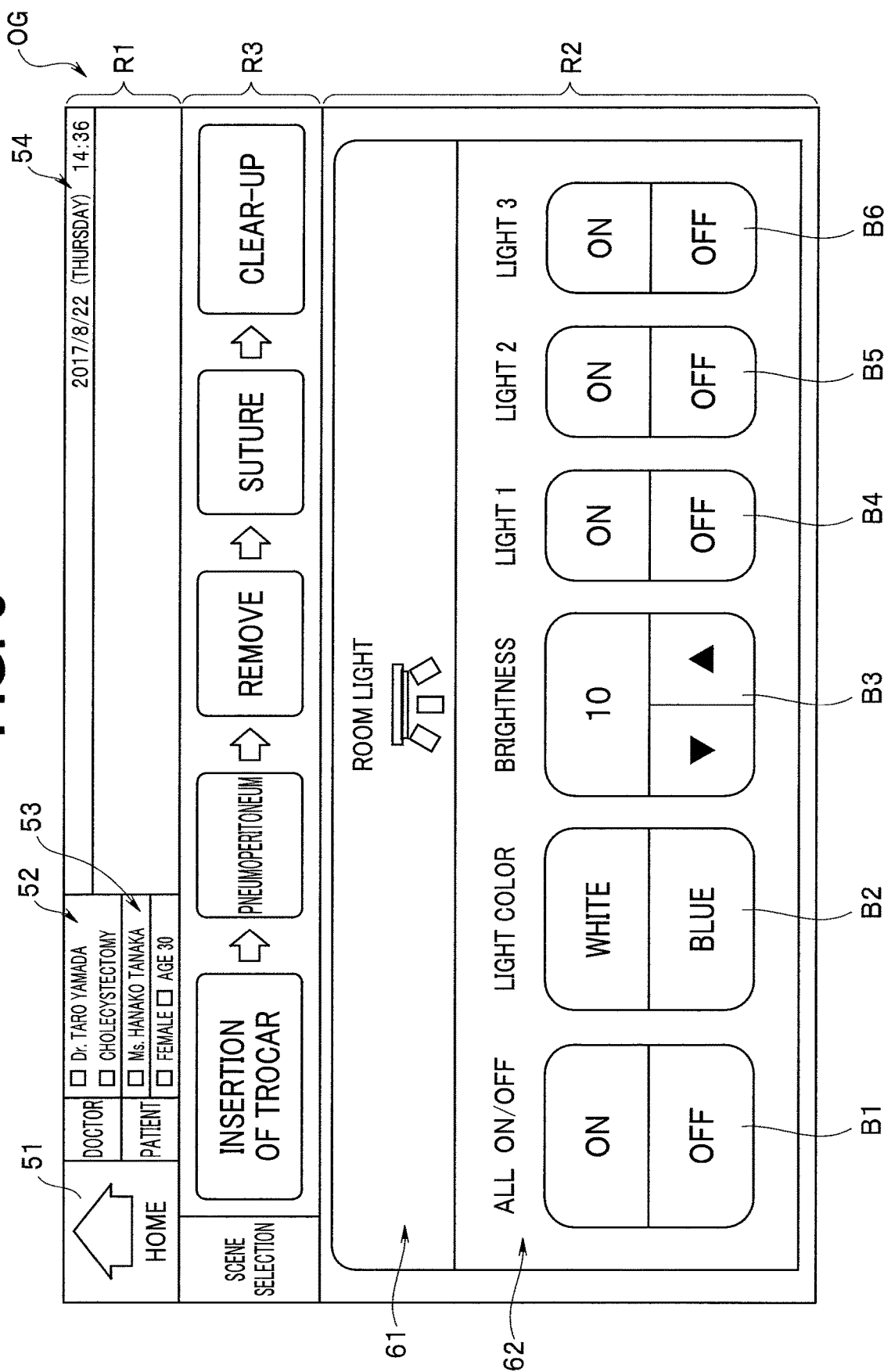
FIG. 6 is a view showing an example of an operation screen according to the embodiment of the present invention.

FIG. 6 is a view showing an example of the operation screen. FIG. 6 shows the operation screen of the room light 7. FIG. 6 is an operation screen which is displayed when the user selects or touches the icon I1 of the room light 7 shown in FIG. 3.

In the lower region R2 of the operation screen OG, an icon display section 61 which displays a character and the icon of the room light 7, and a display/operation section 62 which performs an ON/OFF operation of the room light 7, performing or stopping of the respective functions, an operation of setting set values relating to the functions and the like are displayed. In such a configuration, in the display/operation section 62, the following operation buttons B1 to B6 of the room light 7 are displayed. The operation button B1 makes all of three room lights included in the room light 7 turned on or off. The operation button B2 makes light color white or blue. The operation button B3 operates a level of brightness. The operation button B4 makes the light 1 of three room lights turned on or off. The operation button B5 makes the light 2 of three room lights turned on or off. The operation button B6 makes the light 3 of three room lights turned on or off.

The user can turn on or off the devices, perform functions of the respective devices or can change set values by operating desired operation buttons.

The user can display the home screen HG on the operation panel apparatus 21 by operating, that is, by touching the home button 51. Accordingly, when the user further performs a functional operation with respect to other device, the user returns to the home screen HG, and selects or touches the other device displayed on the home screen HG so that the user can perform the operation of a function which other device has.

Accordingly, the user can change the operation screen from the home screen HG to the operation screen OG of the desired device as indicated by an arrow A1 in FIG. 5, performs an operation with respect to the device, and can change the operation screen from the operation screen OG to the home screen HG as indicated by an arrow A2.

When the user performs the scene selection in a state where the home screen HG is displayed, collective setting processing is performed with respect to the scene.

Returning to FIG. 4, the control unit 41 judges whether or not the scene selection button which is the collective setting button is operated (step (hereinafter abbreviated as S) 1). More specifically, the control unit 41 judges whether or not any one of five icons SI1 to SI5 in the scene selection operation section 55 in FIG. 3 is selected (that is, touched).

When the collective setting button is not operated (S1: NO), no processing is performed.

When the icon I1 "insertion of trocar" in FIG. 3 is selected or touched (S1: YES), the control unit 41 performs collective setting with respect to the scene "insertion of trocar" (S2). Accordingly, processing in S2 performed by the control unit 41 constitutes the collective setting section which performs collective setting processing where setting with respect to one or more controlled devices including a medical device is collectively performed. Processing in S2 is performed in accordance with a collective setting processing program stored in the program storing section 42a.

In S2, the control unit 41 reads set information on the scene "insertion of trocar" from the set information storing section 42b, and sets the read set information in one or more devices relating to the set information.

In step S2, the control unit 41 also performs processing of displaying a screen for notifying the user of a state that the collective setting is underway on the operation panel apparatus 21 when the collective setting is underway with respect to the scene "insertion of trocar".

Figure 7:
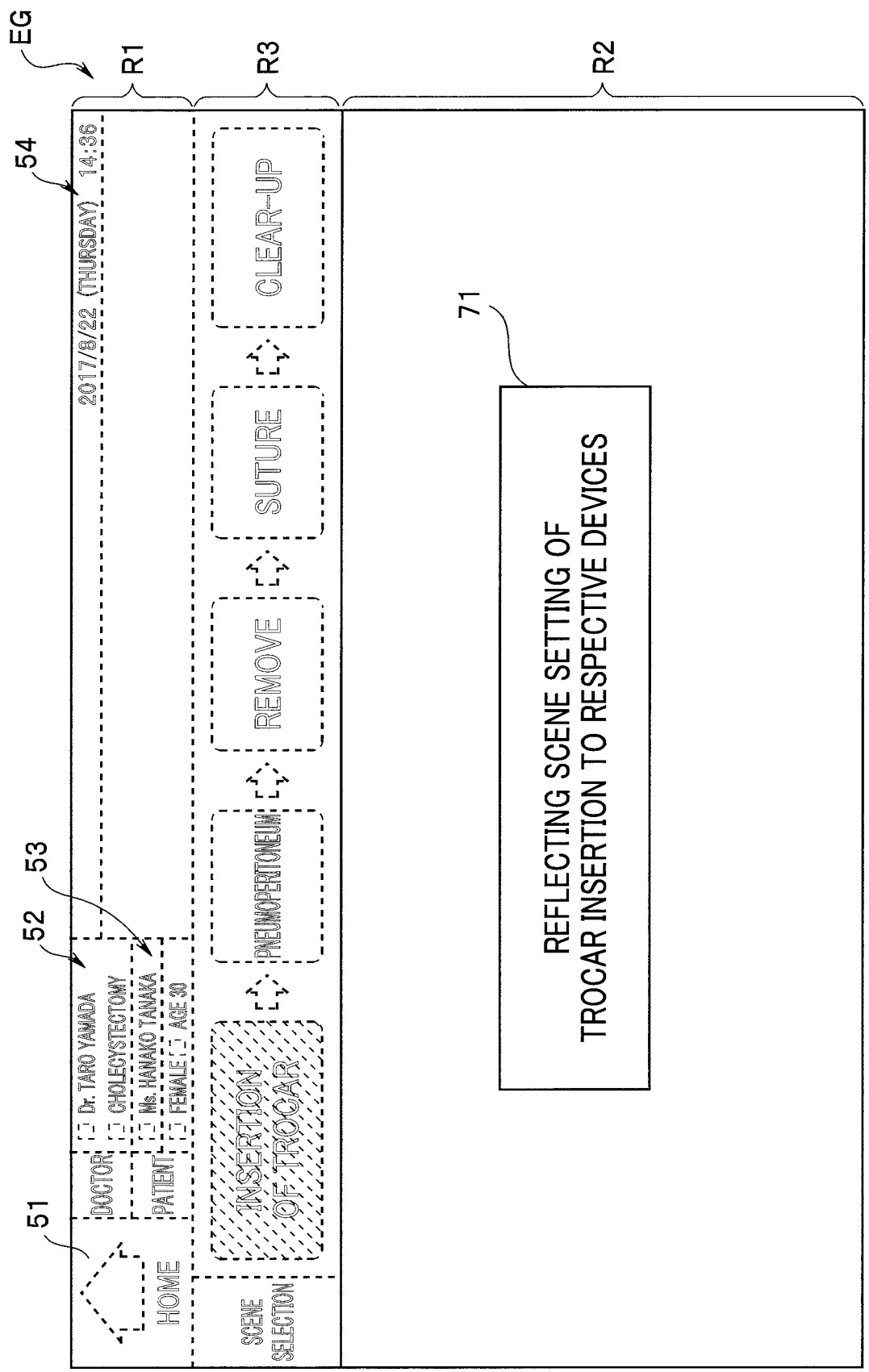
FIG. 7 is a view showing an example of a collective setting underway notification screen for notifying a user that the collective setting is underway according to the embodiment of the present invention.

FIG. 7 is a view showing an example of a collective setting underway notification screen for notifying the user of a state that the collective setting is underway. FIG. 7 shows the collective setting underway notification screen EG displayed on the operation panel apparatus 21 when collective setting processing is underway with respect to the scene "insertion of trocar". A pop-up window 71 is displayed in the lower region R2, and a message display indicating that the collective setting is underway with respect to the scene "insertion of trocar" is displayed on the pop-up window 71.

To inform the user of a state that operations with respect to the upper region R1 and the intermediate region R3 cannot be performed when the collective setting is underway, the upper region R1 and the intermediate region R3 are displayed in a state where brightness is lowered, and only the lower region R2 is brightly displayed by an emphasis display. In FIG. 7, a state that the upper region R1 and the intermediate region R3 are displayed darkly is expressed by indicating lines in the upper region R1 and the intermediate region R3 using a dotted line, and by outlining characters in the upper region R1 and the intermediate region R3.

Accordingly, when the user performs the scene selection, the collective setting underway notification screen EG is displayed as indicated by an arrow A3 in FIG. 5 so that the user can recognize that the collective setting with respect to the scene which the user selects is underway.

When the collective setting processing is finished, the control unit 41 judges whether or not an error occurs (S3). When an error occurs in step S3, such error is error with respect to the collective setting processing, and is also error that setting cannot be performed with respect to a device when the collective setting processing is performed or error that a state of the device does not satisfy a predetermined condition or the like.

When an error occurs (S3: YES), the control unit 41 judges a degree of the occurred error (S4).

FIG. 8 is a graph showing the configuration of a table of the error degree information storing section 42d.

In the embodiment, the error degree information storing section 42d includes a table TBLa where a degree of error is divided in two stages for every error of each device. In the error degree information storing section 42d, as described above, information on the degree of error for every error is set and stored by the user.

For example, with respect to error that a white balance of the video processor 15 is not adjusted, a degree of error is set "large". With respect to error that a limit of a lifetime of a lamp of the light source apparatus 16 is near, the degree of error is set "small".

As described later, by setting the degree of error "small", even when such error occurs after the collective setting is performed, it is unnecessary to perform the removing of such error. Further, by setting the degree of error "large", when such error occurs after the collective setting is performed, the removing of the error can be performed immediately. In other words, by setting the degree of error, the user can set whether or not the removing of error is to be performed immediately after the collective setting is performed.

As described above, the control unit 41 judges the degree of the occurred error by looking up the table TBLa of the error degree information storing section 42d. Accordingly, processing in step S4 of the control unit 41 constitutes the error degree judgement section which judges degrees of errors relating to states of one or more controlled devices which occurred when collective setting processing is performed.

In the embodiment, the state of the controlled apparatus includes ON/OFF, a set value, a displacement amount and the like. The ON/OFF means whether or not a device is in an ON state or in an OFF state, the set value means a set value of an output signal of a device or a set value of a threshold value of the device, the displacement amount is an offset value of a detection value from a reference value or the like.

Error includes a case where a power source of a device is in an OFF state, a case where a device is inoperable, a case where a device is not properly operated, a case where predetermined setting is not performed with respect to a device, a case where a storage capacity or the like is equal to or below a predetermined reference value or below and the like.

When the degree of an occurred error is "large", the control unit 41 generates an error removing screen which is an operation screen and displays the error removing screen (S6). The error removing screen is generated by a screen generating program. As shown in FIG. 5, the operation screen is changed from the home screen HG to the error removing screen ECG via the collective setting performing underway notification screen EG.

In other words, when the degree of the occurred error is "large", to perform the treatment of the scene "insertion of trocar", it is necessary to remove the error. In other words, error is expected to be removed so that the control unit 41 displays the error removing screen for performing the setting or the operation for removing the error on the operation panel apparatus 21.

Figure 9:
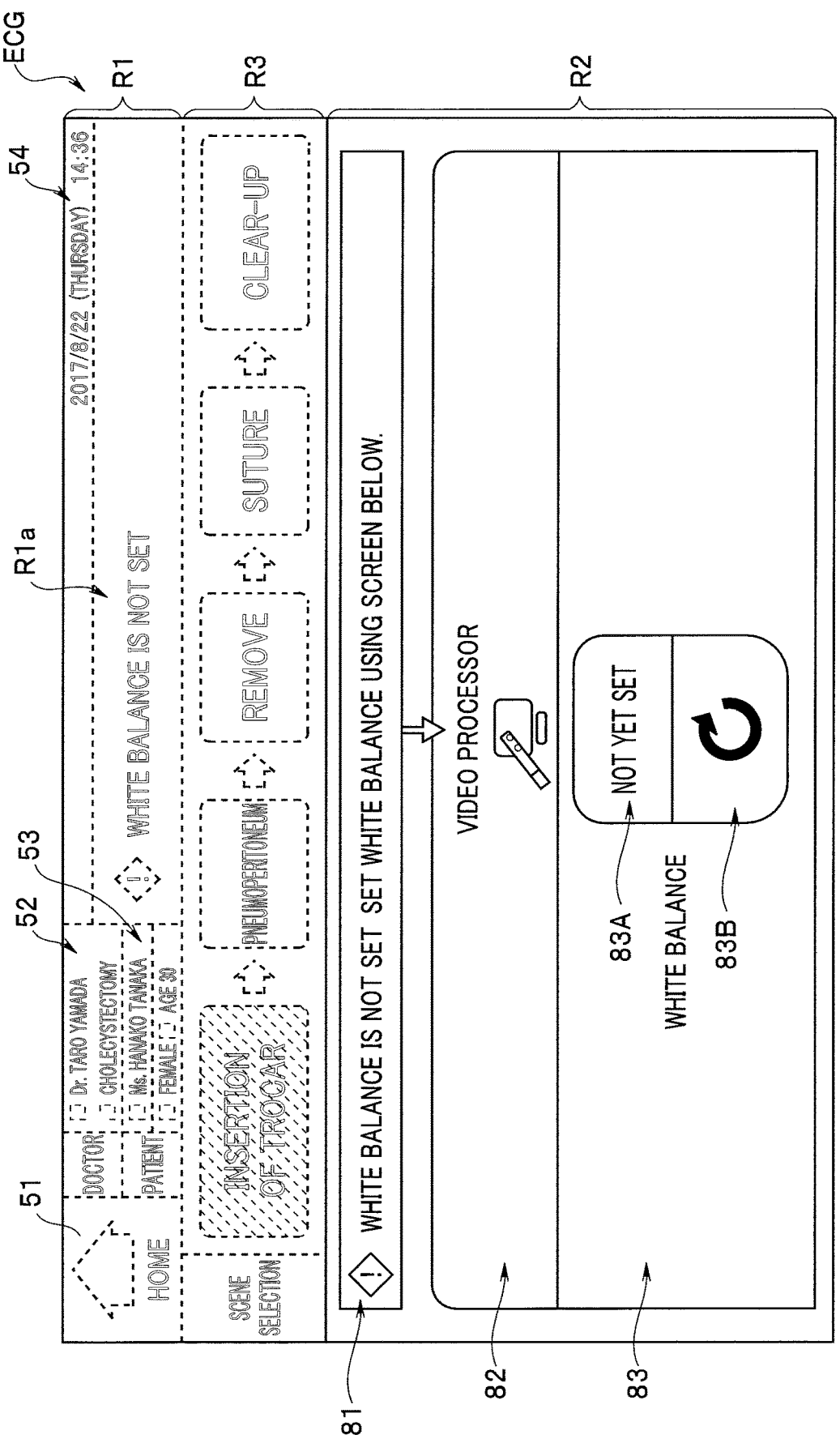
FIG. 9 is a view showing an example of an error removing screen according to the embodiment of the present invention.

FIG. 9 is a view showing an example of the error removing screen. FIG. 9 shows an adjustment screen of a white balance.

On the error removing screen ECG which is the operation screen, an explanation section 81 which explains the content of error and the set content to be performed; a device display section 82 which displays the device to be set; and a display/operation section 83 which displays and performs a set state are displayed. The display/operation section 83 includes a set state display section 83A and an operation instruction section 83B. There may be a case where the device display section 82 is not displayed in the lower region R2.

An error message and a message on the set content to be performed are displayed on the explanation section 81. In the embodiment, an indication that a white balance is not set and a message for instructing setting of the white balance are displayed on the explanation section 81.

An error message may be displayed also in a region R1a which is a portion of the upper region R1 as indicated by a dotted line in FIG. 9.

In the device display section 82, it is displayed by a character and an icon that a device which performs setting of a white balance is a video processor.

In the display/operation section 83, a character to which a white balance is applied is displayed. On the set state display section 83A, a character "not yet set" which indicates that a white balance is not set is displayed. An icon of a setting button is displayed on the operation instruction section 83B. By operating or touching the setting button on the operation instruction section 83B, white balance setting is performed.

As described above, when a user performs the scene selection, the collective setting underway notification screen EG is displayed. When an error of a large degree that a white balance is not set occurs, as indicated by an arrow A4 in FIG. 5, an error removing screen ECG which is an operation screen for setting a white balance is displayed. Accordingly, a user can immediately set a white balance without performing an operation of changing a screen where a user returns to the home screen HG and displays an operation screen for setting a white balance of the video processor.

Setting of a white balance is performed, for example, by mounting a cap for white balance adjustment on a distal end portion of the insertion section of the endoscope 31 and by touching the operation button of the operation instruction section 83B, and set value information obtained by such performance is stored in the video processor 15.

Also in the error removing screen ECG shown in FIG. 9, in the same manner as FIG. 7, to notify a user that the operation cannot be performed in the upper region R1 and the intermediate region R3, the upper region R1 and the intermediate region R3 are displayed darkly, and the lower region R2 is brightly displayed by an emphasis display.

When the error removing screen ECG is displayed, a user can perform an operation for error removing.

The control unit 41 can judge whether or not error removing is completed by monitoring an operation when the error removing screen ECG is displayed (S7).

Until the error removing is completed (S7: NO), no processing is performed.

When the error removing is completed (S7: YES), subsequently, the control unit 41, after the collective setting is performed, estimates an operation that a user uses at high frequency as indicated by an arrow A5 in FIG. 5 by looking up the history information storing section 42c (S8), and displays an operation screen of the estimated operation on the operation panel apparatus 21 (S9).

Figure 10:
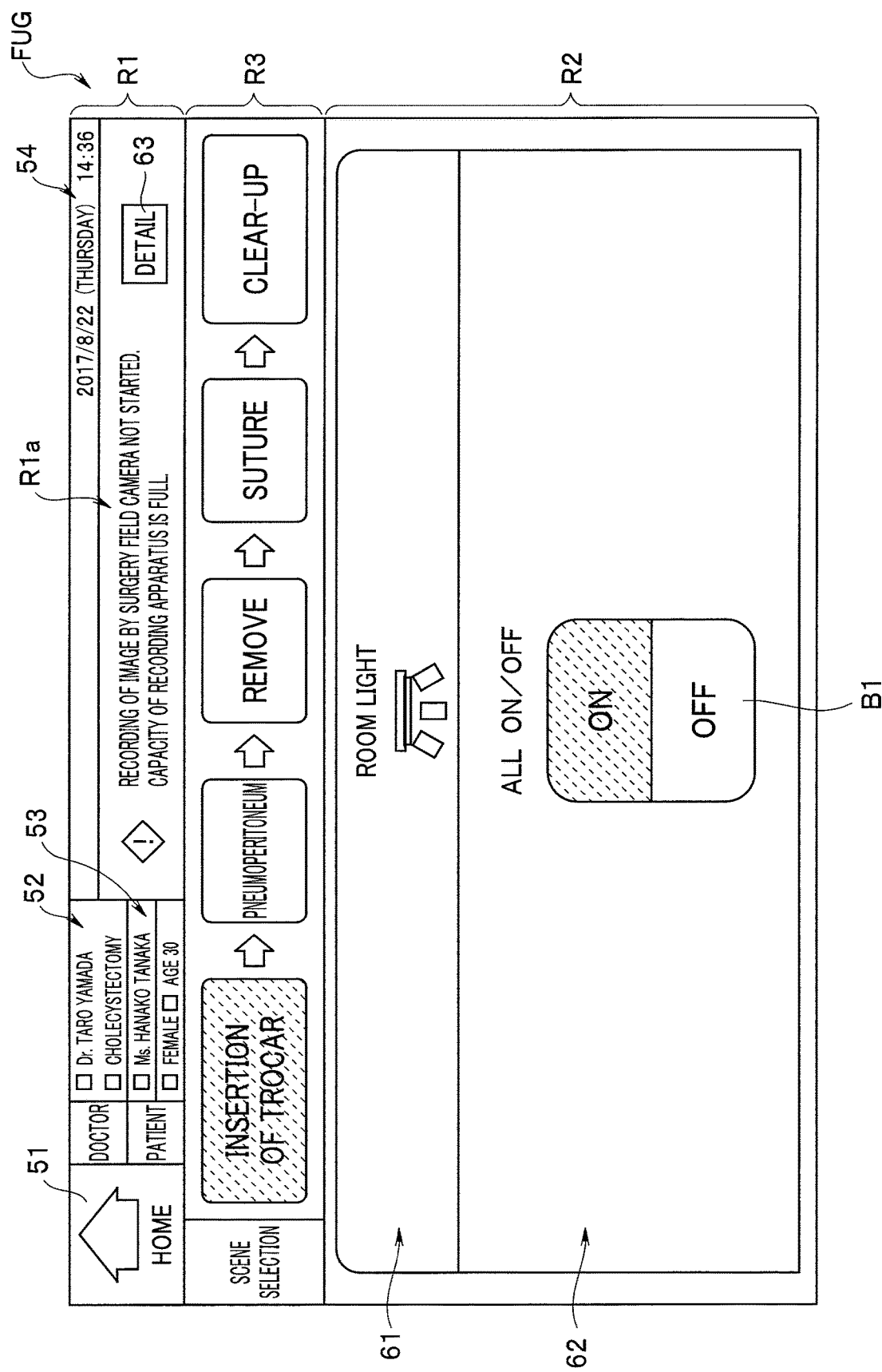
FIG. 10 a view showing an example of a high use frequency function operation screen according to the embodiment of the present invention.

FIG. 10 is a view showing an example of a high use frequency function operation screen. FIG. 10 shows an operation screen of the room light 7 as the high use frequency function operation screen FUG which is an operation screen having a high use frequency function.

In the lower region R2 of the high use frequency function operation screen FUG, an icon display section 61 which displays an icon of the room light 7 and a display/operation section 62 are displayed. In the embodiment, in the display/operation section 62, the operation button B1 for making all three lights of the room light 7 turned on or off is displayed.

A user can turn on or off all three room lights by operating the button B1.

When an error does not occur at the time of performing collective setting (S3: NO), as indicated by an arrow A6 in FIG. 5, the screen is changed from the collective setting underway notification screen EG to the high use frequency function operation screen FUG.

When an error of a small degree occurs at the time of performing collective setting (S5: small), the error removing screen ECG is not displayed. However, as shown in FIG. 10, the content of the error may be displayed in a region R1a of the high use frequency function operation screen FUG.

In FIG. 10, the explanation of the occurred error of a small degree and a button 63 for displaying the content are displayed in the region R1a. A user can acquire detailed information of the error by operating or touching the button 63. In other words, the user can take an action such as error removing when necessary by knowing the presence of the error of a small degree.

The operation screen which the user uses at high frequency after collective setting is performed is determined by analyzing data of the history information storing section 42c.

As described above, operation log information for every user is stored in the history information storing section 42c, and the operation log information includes not only operation information for instructing performing of the collective setting of the scene but also operation information after the collective setting is performed.

Accordingly, after the performing of the collective setting which is performed corresponding to the scene selection is finished, the control unit 41 estimates the operation which the user uses at high frequency from the past history information (S8). In S8, the operation screen which the user uses at calculated high frequency is displayed on the operation panel apparatus 21(S9).

For example, in the case shown in FIG. 3, the scene "pneumoperitoneum" comes after the scene "insertion of trocar". Accordingly, after S2, the control unit 41 extracts the operations performed after the collective setting processing of "insertion of trocar" is performed and before collective setting processing of "pneumoperitoneum" is performed from history information on the procedure of the user during treatment from S3 to S7, and calculates the number of times that each extracted operation is performed. In the embodiment, each operation is an operation for performing one function among various functions which each device has. Accordingly, the control unit 41 calculates the number of times that the respective functions are used during a period after the collective setting processing of "insertion of trocar" is performed and before the collective setting processing of "pneumoperitoneum" is performed.

Assuming the scene selection of "insertion of trocar" as the first setting instruction operation and the scene selection of "pneumoperitoneum" as the second setting instruction operation, processing in S8 constitutes an operation estimation section which estimates operations performed with respect to functions which one or more controlled devices have between the first setting instruction operation performed for the collective setting processing and the second setting instruction operation performed after the first setting instruction operation based on operation log information.

The operations estimated in S8 are operations for performing functions which one or more controlled devices have. Particularly, in S8, the operation which the user uses at high frequency among the plurality of operations performed between the first setting instruction operation and the second setting instruction operation is extracted from past operation log information recorded in the operation log information storing section 42c.

Figures 11, 12:
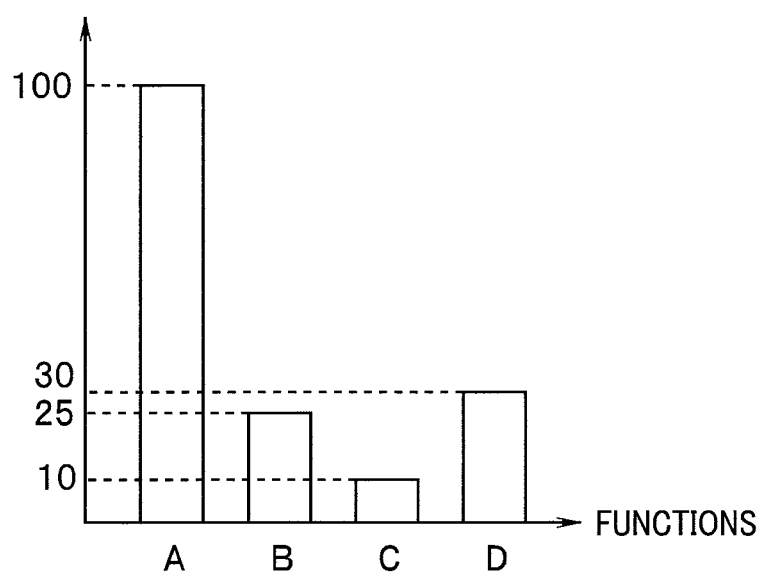
FIG. 11 is a view showing the configuration of a table which is a number-of-use-times table obtained by calculating the number-of-use-times of extracted respective functions according to the embodiment of the present invention.
FIG. 12 is a graph showing the number-of-use-times of four functions shown in FIG. 11.

FIG. 11 is a view showing the configuration of a table TBLb which is a number-of-use-times table. The table TBLb is obtained by calculating the number of use times of extracted respective functions.

The control unit 41 extracts the functions which are used during a period after the collective setting processing of "insertion of trocar" is performed and before the scene selection of "pneumoperitoneum" is performed from past history information stored in the history information storing section 42c, and calculates the number of use times of each extracted function, and prepares the table TBLb shown in FIG. 11.

In other words, the table TBLb includes information on the cumulative performed number of times of the respective functions which are selected and performed by a user during a period after performing collective setting processing with respect to the selected scene to the selection of the scene next to the selected scene.

The table TBLb is prepared for every surgeon and every procedure. However, the table TBLb may not be prepared for every surgeon.

FIG. 11 shows that the function A is performed 100 times, the function B is performed 25 times, the function C is performed 10 times, and the function D is performed 30 times.

Assuming that the table TBLb is prepared by extracting four functions A to D shown in FIG. 11, the function A is most frequently used, the function C is next frequently used, and then, the function B and the function C are used in this order.

FIG. 12 is a graph showing the number of use times of four functions shown in FIG. 11. As shown in FIG. 12, the function A exhibits the largest number of use times.

Assuming that the function A is the device operation of the room light 7, in S8, the above-mentioned operation screen shown in FIG. 10 is displayed.

In the embodiment, one function, the number of use times of which is largest, is selected from the operation history, is displayed and is operable. However, a plurality of functions which belong to an upper group in terms of the number of use times may be selected and displayed.

Figure 13:
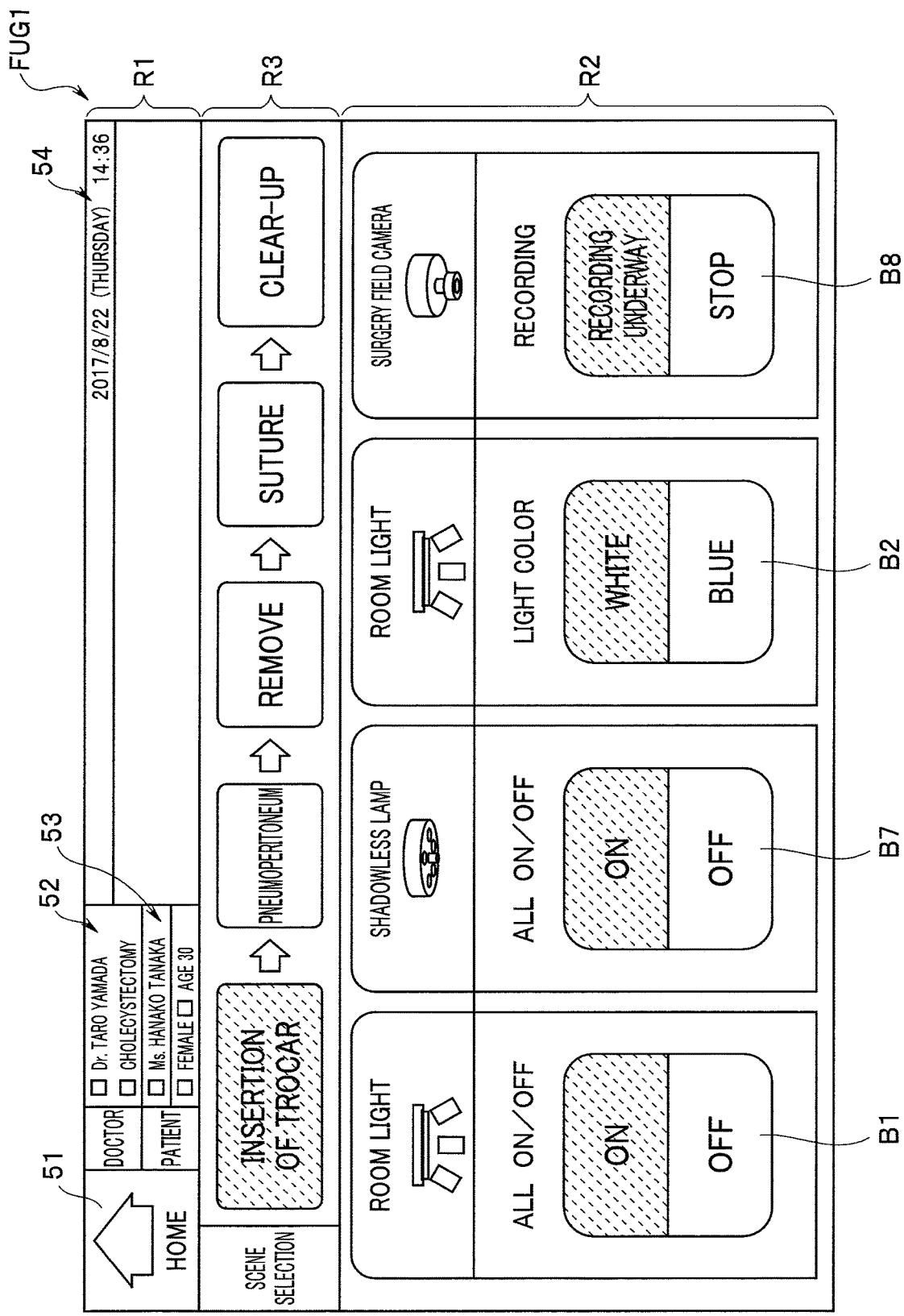
FIG. 13 is a view showing an example of an operation screen which shows a plurality of functions having high use frequency according to the embodiment of the present invention.

FIG. 13 is a view showing an example of an operation screen displaying a plurality of functions which are used at high frequency. A high use frequency function operation screen FUG1 shown in FIG. 13 is an operation screen for four functions belonging to the upper group. More specifically, the operation buttons B1, B7, B2 and B8 are displayed. The operation button B1 is a button for making all three room lights of the room light 7 turned on or off. The operation button B7 is a button for making all shadowless lamps 3 turned on or off. The operation button B2 is a button for making light color white or blue. The operation button B8 is a button for instructing performing or stopping the recording of a surgery field camera (not shown).

Accordingly, a user can perform an operation for a plurality of devices.

An operation screen of an operation, the number of use times of which is a predetermined number or more, may be displayed. When there is no operation screen where the number of use times is more than the predetermined number of times, processing in S8 is not performed.

There may be a case where a user performs error removing by displaying the operation screen for removing error although the operation screen, the use frequency of which is high, is displayed due to processing in S8 and S9.

For example, in the case where the user judges that such error is error which requires an action of the user with priority compared to continuing of a surgery, an operation to display error removing screen for such error is performed. A display operation of the error removing screen is recorded as an operation history. Accordingly, when the number of times of displaying of the error removing screen is increased, number of use times of the error removing function is increased, and the error removing screen is displayed as an operation screen, the frequency of use of which is high, in S9.

After processing in S9 is performed, the control unit 41 judges whether or not the next scene selection button is operated, that is, whether or not the collective setting button is operated (S10).

For example, the scene selection of "pneumoperitoneum" is performed after the scene selection of "insertion of trocar" (S10: YES), the processing advances to S2 where the collective setting processing of the scene "pneumoperitoneum" is performed. Processing in succeeding steps is performed in the same manner as the case of the above-mentioned scene "insertion of trocar".

When collective setting processing in the scene "pneumoperitoneum" is performed as indicated by an arrow A7 in FIG. 5, a collective setting underway notification screen EG is displayed in the same manner as FIG. 7.

Figure 14:
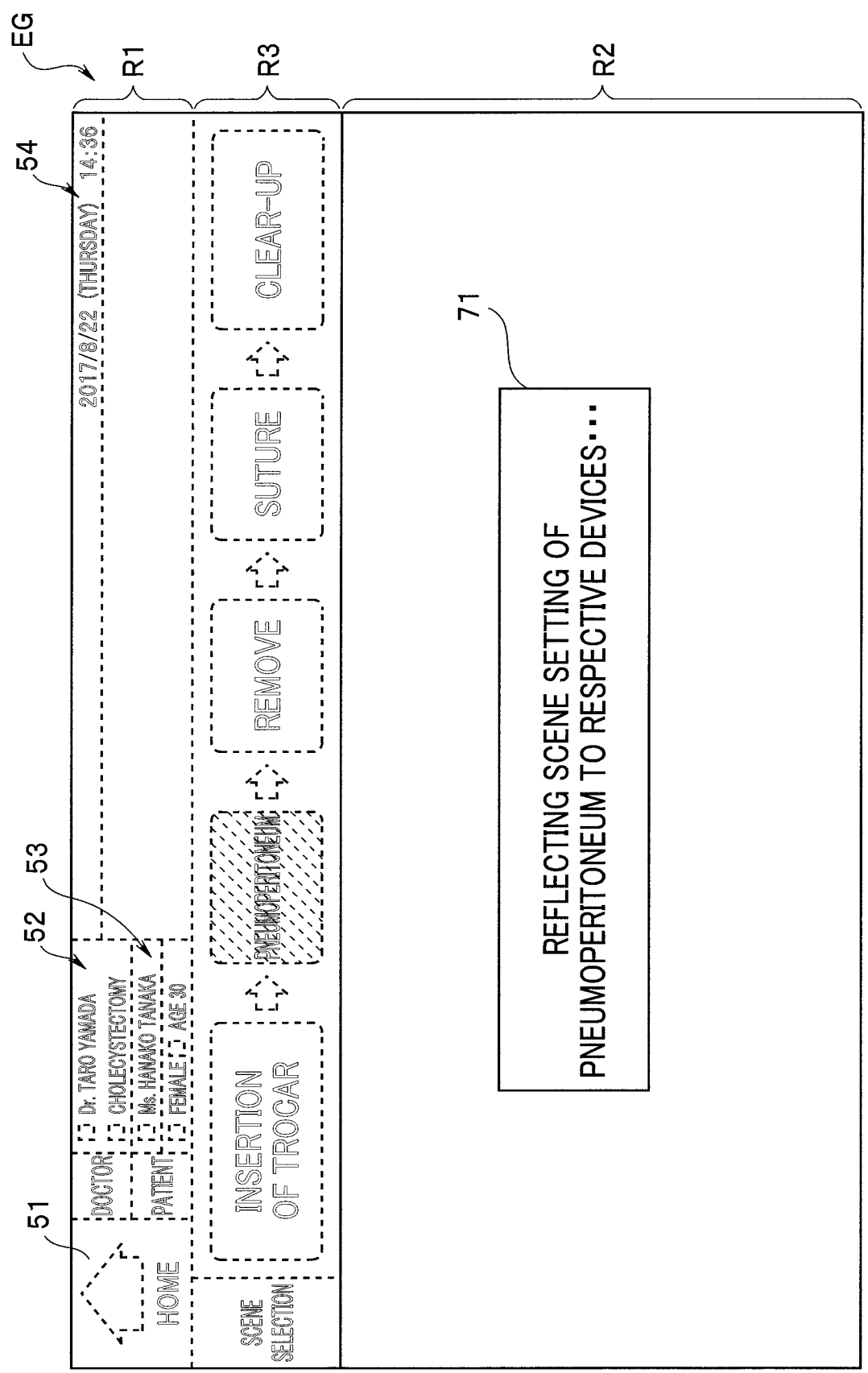
FIG. 14 a view showing a collective setting processing underway notifying screen which is displayed on an operation panel apparatus when collective setting treatment is underway with respect to a scene "pneumoperitoneum" according to the embodiment of the present invention.

FIG. 14 is a view showing the collective setting underway notification screen EG which is displayed on the operation panel apparatus 21 during a period where the collective setting processing is performed with respect to the scene "pneumoperitoneum". A pop-up window 71 is displayed in the lower region R2, and a message display that collective setting is underway with respect to the scene "pneumoperitoneum" is displayed in the pop-up window 71.

When the scene selection button is not operated after processing in S10 (S10: NO), no processing is performed.

In the case where error occurs when collective setting is performed with respect to the scene "pneumoperitoneum" after the scene "insertion of trocar" (S3: YES), an error removing screen for such error is displayed (S6), and the user can immediately perform error removing processing.

After the collective setting and the error removing, the operation screen of the function, the use frequency of which is high, is displayed in the scene "pneumoperitoneum" by the user (S9), and the user can immediately perform the operation.

With respect to the respective scenes, that is, "removing", "suture" and "clear-up" which come after the scene "pneumoperitoneum", substantially the same processing as the above-mentioned "insertion of trocar" and "pneumoperitoneum" are also performed. Accordingly, a user can rapidly take a necessary action even when an error occurs at the time of performing collective setting, and also an operation to display an operation screen, the use frequency of which is high, also becomes unnecessary. Accordingly, the user can perform a surgery rapidly.

As described above, due to processing from S1 to S10 in FIG. 4, when an error occurs in collective setting, an operation screen for performing error removing is displayed and hence, the user can immediately perform error removing. Further, when no error occurs in collective setting or error is removed, an operation screen, the use frequency of which is high, is displayed and hence, the user can immediately perform the next operation.

Processing in S6 and processing in S9 constitute a screen display control section which displays an error removing screen ECG for removing an occurred error based on a judgement result in S4 or an operation screen for performing an operation estimated in S8.

Then, in S4, it is judged whether the degree of an occurred error is "large" which is the first level or "small" which is the second level lower than the first level. In S9, when no error occurs or when the judgement result of error is that the degree of error is "small", an error removing screen is not displayed, and an operation screen of an operation estimated in S8 is displayed.

According to the above-mentioned embodiment, it is possible to provide a centralized control apparatus which can eliminate or reduce time and efforts for an operation for changing an operation screen after collective setting.

Next, a modification of the above-mentioned embodiment is described.

(Modification 1)

In the above-mentioned embodiment, the table TBLa where the degree of error is set for every error in a device is used. However, there may be a case where an action to be taken differs even when the same error occurs depending on a scene of a surgery. Accordingly, the table TBLa may include information on a scene for every error.

An instruction operation of collective setting processing is performed by a selection operation with respect to a plurality of scenes set corresponding to the progress of a surgery. In S4, the degree of error is associated with a plurality of scenes, and the degree of an occurred error is judged based on a scene which is underway in a surgery.

According to the modification 1, the necessity of error removing can be changed for every scene even when the same error occurs.

(Modification 2)

In the above-mentioned embodiment, the degree of error is classified in two stages, that is "large" and "small", and in the above-mentioned modification 1, the degree of error may be classified for every scene. However, the degree of error may be classified in three or more stages.

FIG. 15 is a view showing the configuration of a table of an error degree information storing section 42d relating to the modification 2.

In the modification 2, the error degree information storing section 42d includes a table TBLa1 where the degree of error is classified in three stages for every error of each device. The table TBLa1 stores information on degrees for respective errors as described previously.

In the modification 2, every error is classified into in any one of degrees in three stages including "large", "intermediate" and "small".

In the modification 2, "large" and "small" have the same meaning as "large" and "small" as the embodiment. However, "intermediate" means that there exist a case where the error becomes "large" and a case where the error becomes "small".

When the degree of errors is set to "intermediate", it is judged whether error is "large" or "small" in accordance with a judgement condition associated such setting.

For example, in case of error in FIG. 15 that "endoscope is not connected" in "processor", a judgement condition that after performing collective setting of "insertion of trocar", the degree of error in "intermediate" becomes "small" is associated with the setting of "intermediate". Accordingly, the degree of error "endoscope is not connected" becomes "small". This is because even when the endoscope is not connected to the video processor at the time performing collective setting of "insertion of trocar", there is no problem when the endoscope is connected to the video processor before the collective setting of next "pneumoperitoneum" is performed and hence, it is not indispensable to take an action against the error. Accordingly, in case of performing collective setting in the scenes other than the above-mentioned case, the degree of error "intermediate" becomes "large".

In case of error that "there is no remaining capacity in an incorporated HDD" of a "storage apparatus" shown in FIG. 15, a judgement condition that, after performing collective setting of "clear-up", the degree of error in "intermediate" becomes "large" is associated with the setting of "intermediate". Accordingly, the degree of error in "there is no remaining capacity in an incorporated HDD" becomes "large". This is because that, in the scene "clear-up", undesired data are erased in preparation for a next disease case and hence, it is possible to reduce time and efforts required for removing error by treating the degree of error as "large" and by displaying a screen for removing the error. Accordingly, in case of performing collective setting in the scenes other than the above-mentioned case, the degree of error "intermediate" becomes "small".

In other words, the degree of error has at least three levels including: "large" which is the first level; "small" which is the second level lower than the first level; and "intermediate" which is a third level lower than the first level and higher than the second level. In S4, it is judged which level an occurred error is among at least three levels. When the judgement result of error is that the degree of error belongs to the third level, either one of the error removing screen ECG and the operation screen FUG of the estimated operation is displayed based on the judgement condition set in advance.

(Modification 3)

In the above-mentioned embodiment, when a preset error occurs as error of a large degree, the error removing screen is displayed, and a user can immediately perform the error removing operation. However, depending on a user, there may be a case where it is unnecessary to remove error.

Accordingly, in the modification 3, to allow the advancing of next processing without performing error removing, a button which can select the non-use of error removing is disposed on the error removing screen.

Figure 16:
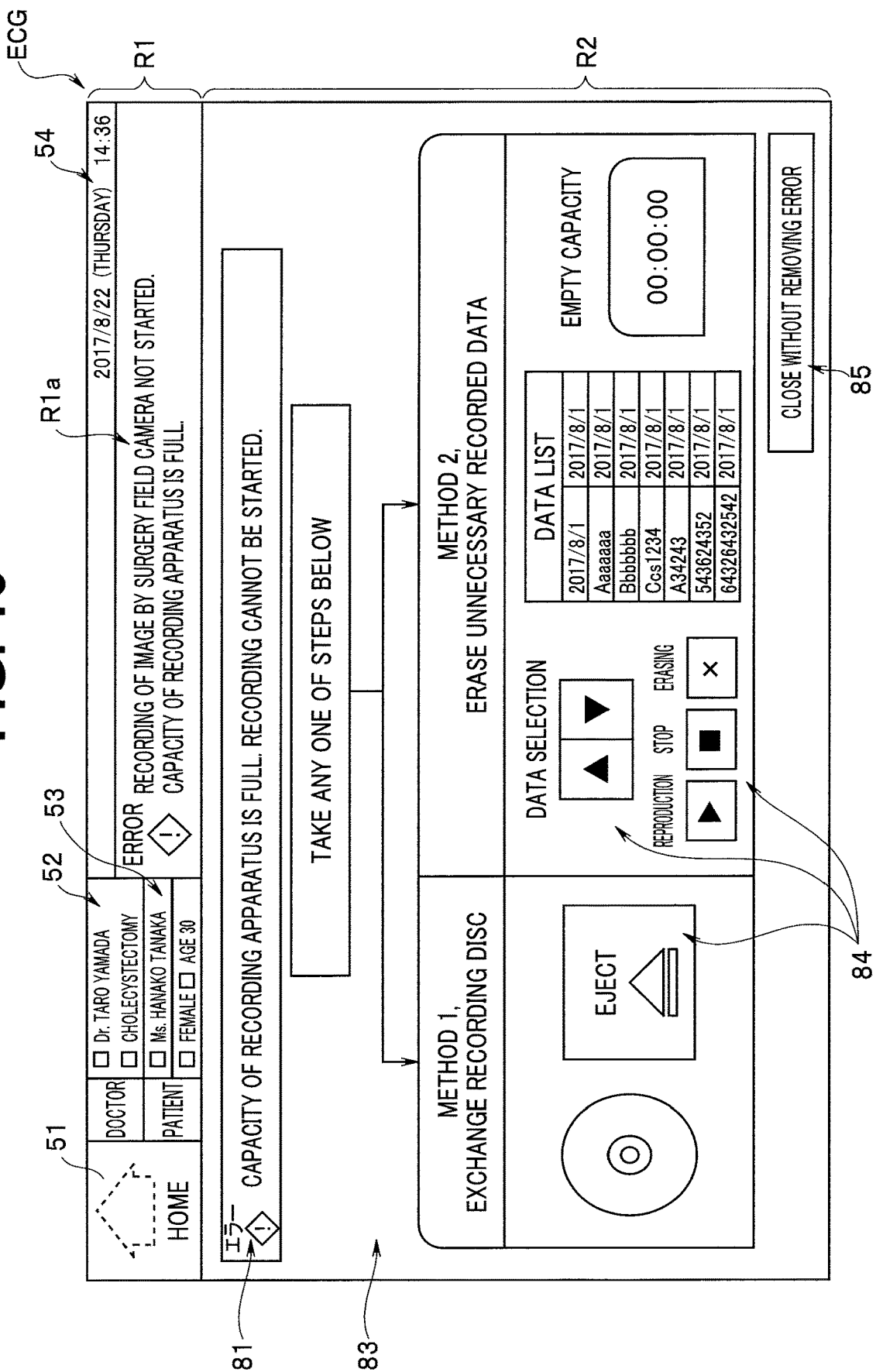
FIG. 16 is a view showing an example of an error removing screen according to a modification 3 of the embodiment of the present invention.

FIG. 16 is a view showing an example of an error removing screen. FIG. 16 shows an error removing screen for error that there is no empty capacity in the recorder 17 which is a recording apparatus. In FIG. 16, an intermediate region R3 is not displayed.

A message "a capacity of a recording apparatus is full so that recording cannot be performed" is displayed on an explanation section 81 in a lower region R2 of the error removing screen ECG. In a display/operation section 83, two methods are proposed as a method of removing error. Various operation buttons 84 are displayed so as to allow a user to select and perform either one of the methods. The error messages are displayed in a region R1a which is a part of an upper region R1.

An error removing non-performing button 85 for selecting non-performing of error removing is disposed on the error removing screen ECG. A character "Closed without removing error" is fixed to the error removing non-performing button 85.

When a user operates or touches the error removing non-performing button 85, the processing advances to processing in S7 in FIG. 4.

In the error removing screen shown in FIG. 16, to notify a user that the home button 51 cannot be operated, the error removing screen is displayed in a state where the brightness is lowered. In FIG. 16, a state that the home button 51 is displayed dimly is indicated such that a line of the home button 51 is expressed by a dotted line and a character of the home button 51 is outlined. This display is adopted to prevent the user from changing the screen to other screen without removing error.

When a plurality of errors exist, an error removing screen ECG for remaining errors is displayed.

As described above, in the modification 3, the error removing screen ECG has an error removing non-performing button 85 as an error removing non-performing operation section for instructing non-performing of error removing. When the error removing non-performing button 85 is operated, error removing processing is not performed.

Accordingly, the user can select processing where error removing is not performed.

(Modification 4)

In the above-mentioned embodiment, when the degree of error occurred in collective setting processing is "large", the error removing screen ECG is automatically displayed. However, an error removing screen in the case the degree of error is "small" is not displayed. If the user wants to change the degree of error where the degree of error is set to "small", in the previously mentioned example, it is necessary to always perform a cumbersome operation of changing the setting of the data in the table TBLa.

In view of the above, in the modification 4, when a user removes error which is set as error of a small degree, the degree of error can be changed with a simple operation.

As described in the above-mentioned embodiment, there may be case where a user performs error removing by calling an operation screen for removing the error although an operation screen, the use frequency of which is high, is displayed due to processing performed in S9.

When such a user removes error of a small degree, necessity of a change of such a degree of error is asked to the user, and the degree of error is changed when the change is necessary.

Figure 17:
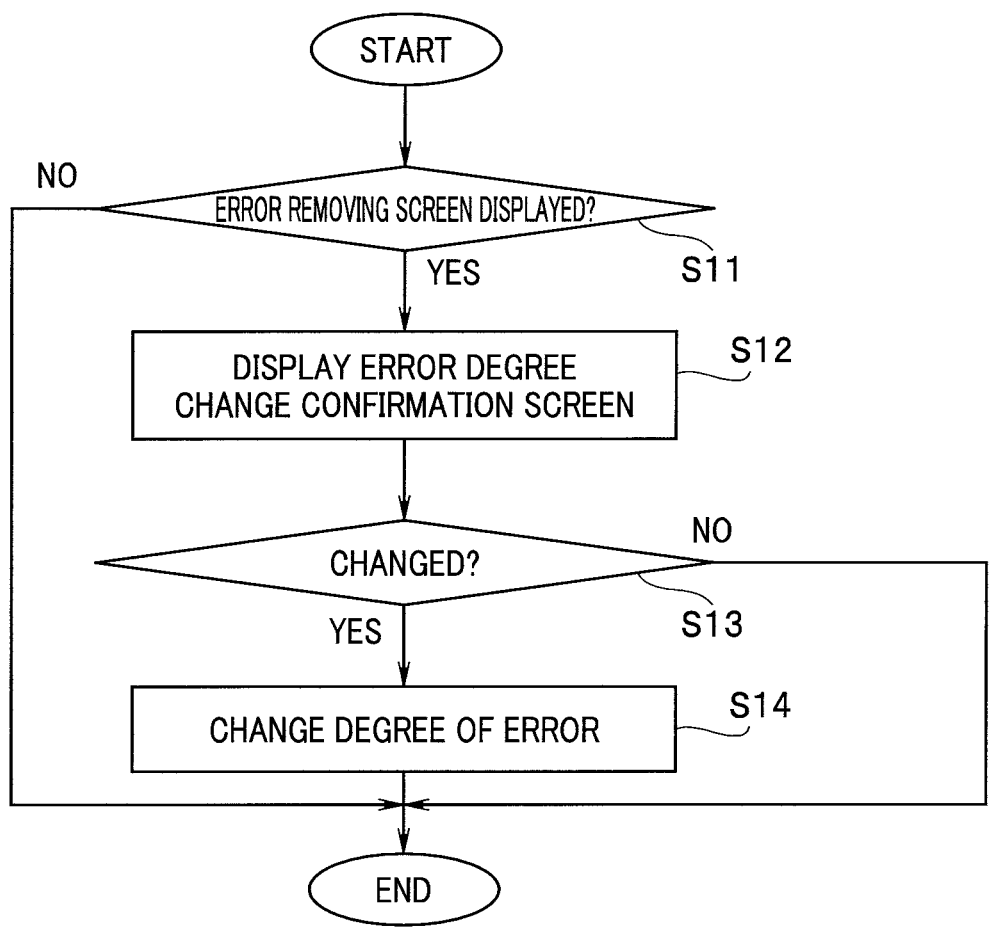
FIG. 17 is a flowchart showing an example of the flow of a degree changing processing for changing a degree of error according to a modification 4 of the embodiment of the present invention.

FIG. 17 is a flowchart showing an example of the flow of degree changing processing for changing the degree of error.

When an operation screen, the use frequency of which is high, is displayed due to processing in S9 shown in FIG. 4, the control unit 41 judges whether or not the user returns to the home screen HG for removing error of a small degree and performs an operation of displaying the error removing screen (S11).

During performing the processing in S9, when the user does not perform reading of the screen for removing error, the error removing screen ECG is not displayed (S11: NO) and hence, no processing is performed.

During performing processing in S9, when the user performs displaying of the screen of removing the error, the error removing screen ECG is displayed (S11: YES) and hence, the control unit 41 displays an error degree change confirmation screen ERCG not shown on the operation panel apparatus 21 (S12).

Although not shown, the error degree change confirmation screen ERCG has a display of a message which asks a user whether or not the degree of error relating to an error removing screen is to be changed to "large", and two operation buttons for making the degree of error changed to "large" or not changed, for example, the "YES" button and the "NO" button.

When the user selects or touches the "YES" button out of two operation buttons, the control unit 41 judges that the degree of error is changed (S13: YES), and performs rewriting of data where the degree of error is set to "large" with respect to the table TBLa (S14).

In other words, the processing performed in S14 constitutes a degree information changing section which displays the error degree change confirmation screen ERCG as a screen for confirming whether or not information on the degree of error is to be changed, and changes the information on the degree of error based on the operation to the displayed confirmation screen.

When the user selects or touches "NO" button out of two operation buttons, it is judged that the degree of error is not changed (S13: YES) and no processing is performed.

Accordingly, in the modification 4, the user can change the degree of error with the simple operation.

In the case where the degree of error is changed to "large", when the error occurs, the error removing screen ECG is displayed, and the user can rapidly perform the error removing.

(Modification 5)

In the modification 4, in the case where the user performs a display operation of the error removing screen for removing error of a small degree when an operation screen, the use frequency of which is high, is displayed, the error degree change confirmation screen is displayed, and the confirmation whether the degree of error is changed from "small" to "large" is performed with respect to the user so that the user can change the degree of error to "large". However, the error, the degree of which is set to "large", may be changed to error, the degree of which is set to "small".

In the above-mentioned embodiment, when an error, the degree of which is set to "large", occurs, the error removing screen ECG is displayed. In the modification 5, the error removing screen ECG includes a button for changing the degree of error to "small".

Figure 18:
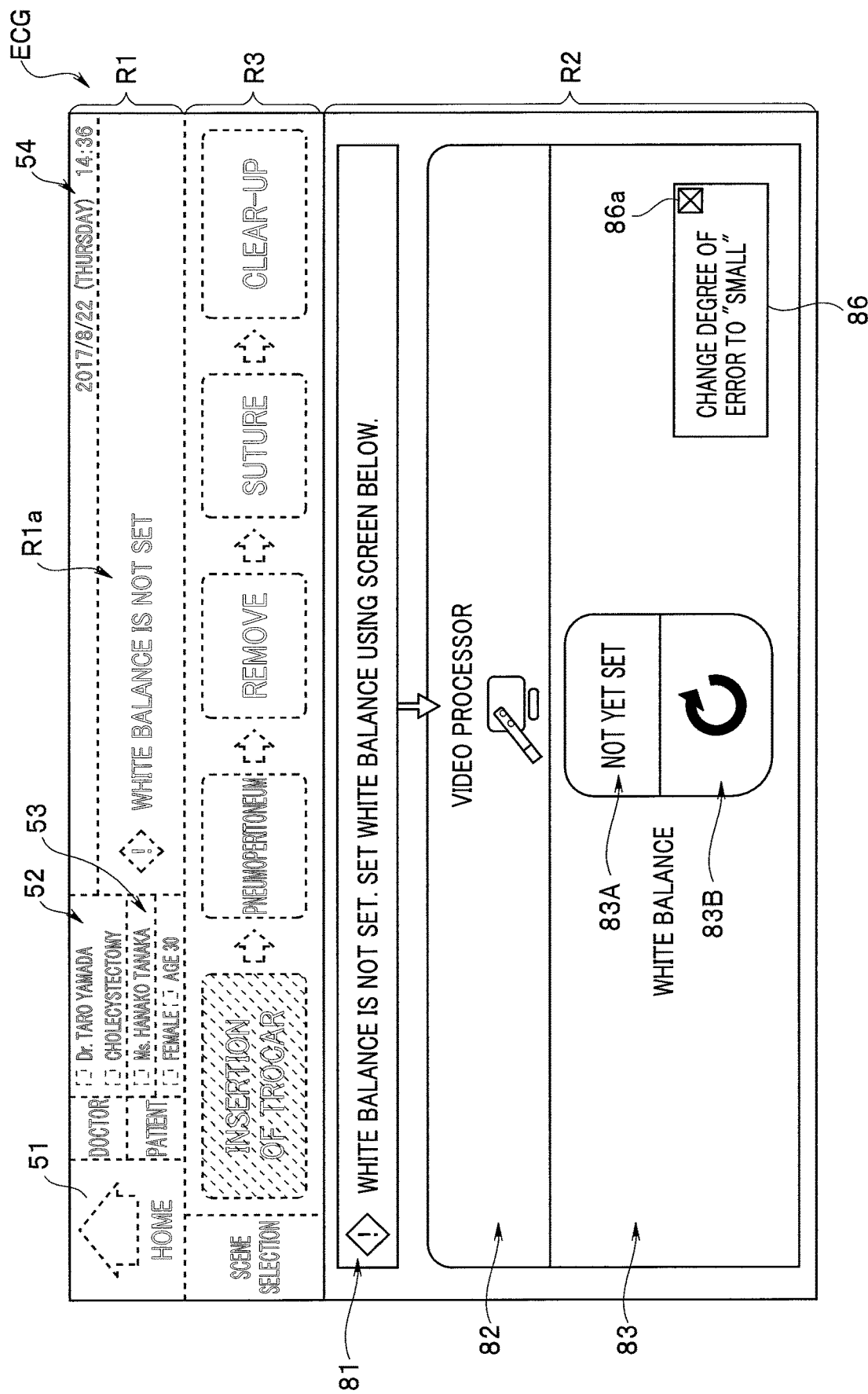
FIG. 18 is a view showing an example of an error removing screen according to a modification 4 of the embodiment of the present invention.

FIG. 18 is a view showing an example of the error removing screen relating to the modification 5. The example shown in FIG. 18 is an adjustment screen of a white balance in the same manner as FIG. 9. However, an error degree change button 86 which changes the degree of error to "small" is displayed as a pop-up window in a lower region R2.

When the user operates or touches the error degree change button 86, the control unit 41 changes the degree of error relating to the displayed error removing screen ECG, in the modification, the degree of error that a white balance is not yet adjusted is changed from "large" to "small". In other words, the control unit 41 performs writing which changes the degree of error, a white balance of which is not yet adjusted, in a table TBLa from "large" to "small".

Accordingly, the error removing screen shown in FIG. 18 forms a confirmation screen whether or not information on the degree of error is to be changed. Processing performed in S22 constitutes a degree information changing section which changes information on the degree of error.

The error degree change button 86 is a button which cancels a display of the error degree change button 86. In FIG. 18, when a user operates or touches a button 86a displayed on a right upper corner of the error degree change button 86, a display of a pop-up window of the error degree change button 86 disappears.

Figure 19:
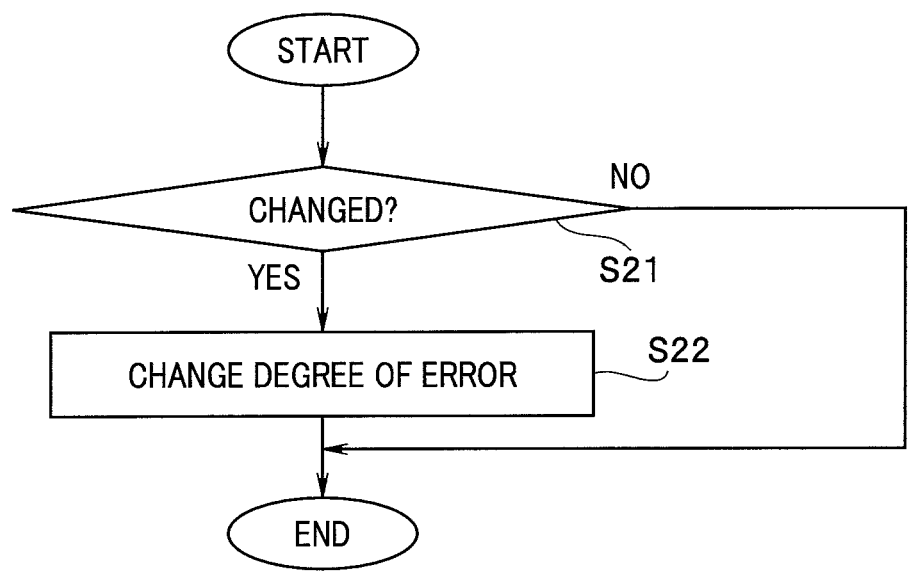
FIG. 19 a flowchart showing an example of the flow of a degree changing processing for changing a degree of error according to a modification 5 of the embodiment of the present invention.

FIG. 19 is a flowchart showing an example of the flow of degree changing processing which changes the degree of error relating to the modification 5.

Processing in FIG. 19 is performed when the error removing screen ECG is displayed. The control unit 41 judges whether or not the error degree change button 86 is operated, that is, whether or not changing of the degree of error is instructed (S21).

When changing of the degree of error is not instructed (S21: NO), no processing is performed. When changing of the degree of error is instructed, that is, when the error degree change button 86 is operated (S21: YES), the control unit 41 changes the degree of error relating to the error removing screen ECG from "large" to "small" (S22).

Accordingly, the user can change the degree of error to "small" so that even when the error occurs, it is possible to prevent the error from being displayed on the error removing screen ECG.

As has been described heretofore, according to embodiment and the respective modifications described above, it is possible to provide a centralized control apparatus which can eliminate or reduce time and efforts for performing an operation of changing an operation screen after collective setting.

The present invention is not limited to the above-mentioned embodiment, and various alterations and modifications are conceivable without departing from the gist of the present invention.

What is claimed is:

1. A centralized control apparatus comprising a processor, the processor being configured to:

perform collective setting processing by receiving an instruction operation which collectively performs setting with respect to one or more controlled devices including a medical device, judge a degree of error relating to a state of the one or more controlled devices which occurs when the collective setting processing is performed due to a setting instruction operation performed with respect to the one or more controlled devices; and control so as to display an error removing screen for removing an occurred error when the degree of error is equal to or more than a predetermined level based on a judgement result of the degree of error, the error removing screen explaining a content of the occurred error and a setting content to be performed, the error removing screen including an operation screen enabling to set a device related to the setting content, wherein the setting instruction operation being an operation for selecting a desired scene from a plurality of scenes set in advance corresponding to a progress of a surgery, wherein the degree of error being associated with the plurality of scenes, and wherein the processor is configured to judge the degree of the occurred error based on a scene which is underway in the surgery.

2. The centralized control apparatus according to claim 1, further comprising a storage apparatus which stores operation information on operations performed with respect to the one or more controlled devices as operation log information, wherein the processor is configured to:

estimate an operation performed with respect to functions which the one or more controlled devices include between a first setting instruction operation performed for the collective setting processing and a second setting instruction operation performed after the first setting instruction operation; and display the error removing screen for removing the occurred error or an operation screen for performing the estimated operation based on the judgement result of the degree of error.

3. The centralized control apparatus according to claim 2, wherein the first and second setting instruction operations are respectively an operation which selects a scene from the plurality of scenes set corresponding to the progress of the surgery.

4. The centralized control apparatus according to claim 2, wherein the estimated operation is an operation for performing functions which the one or more controlled devices include.

5. The centralized control apparatus according to claim 2, wherein the processor is configured to estimate the operation by extracting an operation, use frequency of which is high, from a plurality of operations performed between the first setting instruction operation and the second setting instruction operation from past operation log information recorded in the storage apparatus.

6. The centralized control apparatus according to claim 2, wherein the processor is configured to:

judge whether the degree of the occurred error is a first level or a second level lower than the first level; and display the operation screen of the estimated operation without displaying the error removing screen when there is no occurrence of the error or the judgement result of the degree of error is such that the degree of error is the second level.

7. The centralized control apparatus according to claim 2, wherein the degree of error includes at least three levels including a first level, a second level lower than the first level, and a third level lower than the first level and higher than the second level, the processor is configured to judge which level the degree of the occurred error is among the at least three levels, and the processor is configured to display either one of the error removing screen and the operation screen of the estimated operation based on a judgement condition set in advance when the judgement result of the degree of error is such that the degree of error is the third level.

8. The centralized control apparatus according to claim 1, wherein the error removing screen includes an error removing non-performing operation section for instructing non-performing of the removing of the error.

9. The centralized control apparatus according to claim 1, further comprising a storage apparatus which stores information on the degree of each error, wherein the processor is configured to display a confirmation screen for checking changing of the information on the degree, and to change information on the degree based on an operation with respect to the displayed confirmation screen.

10. A method of controlling one or more controlled apparatuses including a medical device, the method comprising:

performing collective setting processing by receiving an instruction operation which collectively performs setting with respect to the one or more controlled devices;

judging a degree of error which occurs when the collective setting processing is performed due to a setting instruction operation performed with respect to the one or more controlled devices in a state where the degree of error is associated with states of the one or more controlled devices and a plurality of scenes which are underway in a surgery; and controlling so as to display an error removing screen for removing an occurred error when the degree of error is equal to or more than a predetermined level based on a judgement result of the degree of error, the error removing screen explaining a content of the occurred error and a setting content to be performed, the error removing screen including an operation screen enabling to set a device related to the setting content, wherein the setting instruction operation is an operation which selects a desired scene from a plurality of scenes which are set in advance corresponding to a progress of a surgery, wherein the degree of error is associated with the plurality of scenes, and wherein the degree of the occurred error is judged based on a scene which is underway in the surgery.

* * * * *